US009114217B2

(12) United States Patent
Sur et al.

(10) Patent No.: US 9,114,217 B2
(45) Date of Patent: Aug. 25, 2015

(54) PATTERN RECOGNITION SYSTEM AND METHOD FOR THE DETECTION OF STUCK FLUID DROPLETS IN A FLUID DELIVERY LINE OF AN INFUSION SYSTEM

(75) Inventors: Kunal Sur, Evanston, IL (US); Paul T. Kotnik, Commerce, IL (US); Anatoly S. Belkin, Glenview, IL (US); John Hicks Dumas, III, Libertyville, IL (US); Timothy L. Ruchti, Gurnee, IL (US)

(73) Assignee: Hospira, Inc., Lake Forest, IL (US)

( * ) Notice: Subject to any disclaimer, the term of this patent is extended or adjusted under 35 U.S.C. 154(b) by 563 days.

(21) Appl. No.: 13/588,049

(22) Filed: Aug. 17, 2012

(65) Prior Publication Data
US 2013/0046508 A1 Feb. 21, 2013

Related U.S. Application Data

(60) Provisional application No. 61/525,587, filed on Aug. 19, 2011.

(51) Int. Cl.
*G06F 11/30* (2006.01)
*A61M 5/36* (2006.01)
*A61M 5/142* (2006.01)

(52) U.S. Cl.
CPC .............. *A61M 5/365* (2013.01); *A61M 5/142* (2013.01); *A61M 2205/18* (2013.01); *A61M 2205/50* (2013.01)

(58) Field of Classification Search
CPC .. A61M 5/142; A61M 5/365; A61M 2205/18
USPC ............................................. 702/183
See application file for complete search history.

(56) References Cited

U.S. PATENT DOCUMENTS

| 4,981,467 | A | | 1/1991 | Bobo, Jr. et al. |
|---|---|---|---|---|
| 5,053,747 | A | | 10/1991 | Slate |
| 5,059,171 | A | | 10/1991 | Bridge |
| 5,064,412 | A | | 11/1991 | Henke |
| 5,198,776 | A | | 3/1993 | Carr |
| 5,260,665 | A | | 11/1993 | Goldberg |
| 5,394,732 | A | | 3/1995 | Johnson et al. |
| 5,505,696 | A | | 4/1996 | Miki |
| 5,616,124 | A | * | 4/1997 | Hague et al. ............ 604/65 |
| 5,843,035 | A | | 12/1998 | Bowman |
| 6,068,612 | A | | 5/2000 | Bowman |
| 6,408,679 | B1 | * | 6/2002 | Kline-Schoder et al. .... 73/19.03 |
| 6,463,785 | B1 | | 10/2002 | Kline-Schoder |
| 6,467,331 | B1 | | 10/2002 | Kline-Schoder |
| 6,572,576 | B2 | | 6/2003 | Brugger |
| 6,616,633 | B1 | | 9/2003 | Butterfield |
| 6,622,542 | B2 | | 9/2003 | Derek |
| 6,629,449 | B1 | | 10/2003 | Kline-Schoder |

(Continued)

*Primary Examiner* — Janet Suglo
*Assistant Examiner* — Stephanie Bloss
(74) *Attorney, Agent, or Firm* — Michael R. Crabb

(57) ABSTRACT

An infusion system includes a pump, a fluid delivery line, a sensor, a processor, and a memory. The fluid delivery line is connected to the pump for delivering fluid. The sensor is connected to the fluid delivery line for emitting and receiving signals to detect whether there is air in the fluid delivery line. The processor is in electronic communication with the pump and the sensor. The memory is in electronic communication with the processor. The memory includes programming code for execution by the processor. The programming code is configured to analyze the signals to determine if a stuck fluid droplet is stuck within the fluid delivery line at a location of the sensor.

42 Claims, 14 Drawing Sheets

(56) References Cited

U.S. PATENT DOCUMENTS

| | | |
|---|---|---|
| 6,830,558 B2 | 12/2004 | Flaherty et al. |
| 7,141,037 B2 | 11/2006 | Butterfield |
| 7,338,470 B2 | 3/2008 | Katz |
| 7,482,818 B2 | 1/2009 | Greenwald et al. |
| 7,654,127 B2 | 2/2010 | Krulevitch et al. |
| 2005/0192529 A1* | 9/2005 | Butterfield et al. ............ 604/65 |
| 2007/0060874 A1* | 3/2007 | Nesbitt et al. ................... 604/80 |
| 2008/0039777 A1 | 2/2008 | Katz et al. |
| 2008/0098798 A1 | 5/2008 | Riley et al. |
| 2008/0208484 A1 | 8/2008 | Butterfield et al. |
| 2009/0053071 A1* | 2/2009 | Wang et al. ...................... 417/12 |
| 2009/0205426 A1 | 8/2009 | Balschat et al. |
| 2010/0141460 A1 | 6/2010 | Tokhtuev et al. |
| 2010/0212407 A1 | 8/2010 | Stringham et al. |

\* cited by examiner

PATTERN RECOGNITION SYSTEM AND METHOD FOR THE DETECTION OF STUCK FLUID DROPLETS IN A FLUID DELIVERY LINE OF AN INFUSION SYSTEM

FIELD OF THE DISCLOSURE

The disclosure relates to a system and method for detecting air despite the presence of stuck fluid droplets in a fluid delivery line of an infusion system. The disclosure further relates to a system and method for dynamically updating, in real-time, a dynamic range of a sensor voltage signal to more accurately determine the presence of air within a fluid delivery line of an infusion system.

BACKGROUND OF THE DISCLOSURE

Ultrasonic transducer pairs, comprising a transmitter and a receiver, are commonly applied to detect air in a fluid delivery line segment as part of medication infusion systems, such as PLUM A+™, GEMSTAR™ and SYMBIQ™. The sensors are physically located on opposite sides of a fluid delivery line segment and the presence of air in the fluid delivery line causes an acoustical open circuit which substantially attenuates the detected signal. When fluid is present, propagation of the acoustic signal is efficient and produces a large electrical signal via the receiver circuit.

Detection of air in the fluid delivery line segment is typically performed on the basis of a fixed air-fluid boundary or threshold that is applied to the sensor voltage or current signal. Any signal on the fluid side of the threshold is classified as representing the presence of fluid in the infusion line and any signal on the air side of the threshold is classified as representing air. Typically a fixed threshold is applied that is specific to the infusion pump set and sensor arrangement.

When air is infused past the sensor pair, the presence of a stationary fluid droplet that bridges the gap between the transducers may lead to an acoustic short circuit. This can produce an absolute sensor signal similar to that of a fluid and result in a false negative indicating the presence of fluid when air is actually disposed over the sensor. This is problematic because the air sensor signal, indicating that air is in the infusion line, is typically used to produce an air-in-line alarm, to pause the pumping mechanism, and to reduce the potential for the infusion of air into a patient's vascular system.

Additionally, air detection systems in infusion delivery lines typically assume a fixed, constant dynamic range for the sensor voltage signal. However, if the dynamic range of the sensor voltage signal increases, due to typical system variation, the system may become less sensitive to the presence of air within the system. This may lead to the system mistakenly determining that fluid is in the system when air is actually in the system.

An infusion system and method is needed which will accurately determine the presence of a stuck fluid droplet between a sensor pair to indicate the presence of air in the system. Additionally, an infusion system and method is needed which will dynamically update, in real-time, the dynamic range for the sensor voltage signal to more accurately determine the presence of air within the system.

SUMMARY OF THE DISCLOSURE

In one embodiment, an infusion system comprises a pump, a fluid delivery line, at least one sensor, a processor, and a memory. The fluid delivery line is connected to the pump for delivering fluid. The at least one sensor is connected to the fluid delivery line for emitting and receiving signals to detect whether there is air in the fluid delivery line. The processor is in electronic communication with the pump and the at least one sensor. The memory is in electronic communication with the processor. The memory comprises programming code for execution by the processor. The programming code is configured to analyze the signals to determine if a stuck fluid droplet is stuck within the fluid delivery line at a location of the at least one sensor.

In another embodiment, a method is disclosed for detecting a stuck fluid droplet in a fluid delivery line of an infusion system. In one step, fluid is pumped through the fluid delivery line over at least one sensor. In another step, signals are emitted and received from the at least one sensor into and from the fluid delivery line. In yet another step, measurements of the signals are processed, using a processor, to determine whether a stuck fluid droplet is stuck within the fluid delivery line at a location of the at least one sensor.

In yet another embodiment, a method is disclosed for detecting air in a fluid delivery line of an infusion system. In one step, fluid is pumped through the fluid delivery line over at least one sensor. In another step, signals are emitted and received from the at least one sensor into and from the fluid delivery line. In yet another step, measurements of the signals are processed, using a processor, to determine whether the air is within the fluid delivery line by determining a pattern relationship over time of the signals while the signals are below an air/liquid threshold ADV value boundary.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

Figure 1:
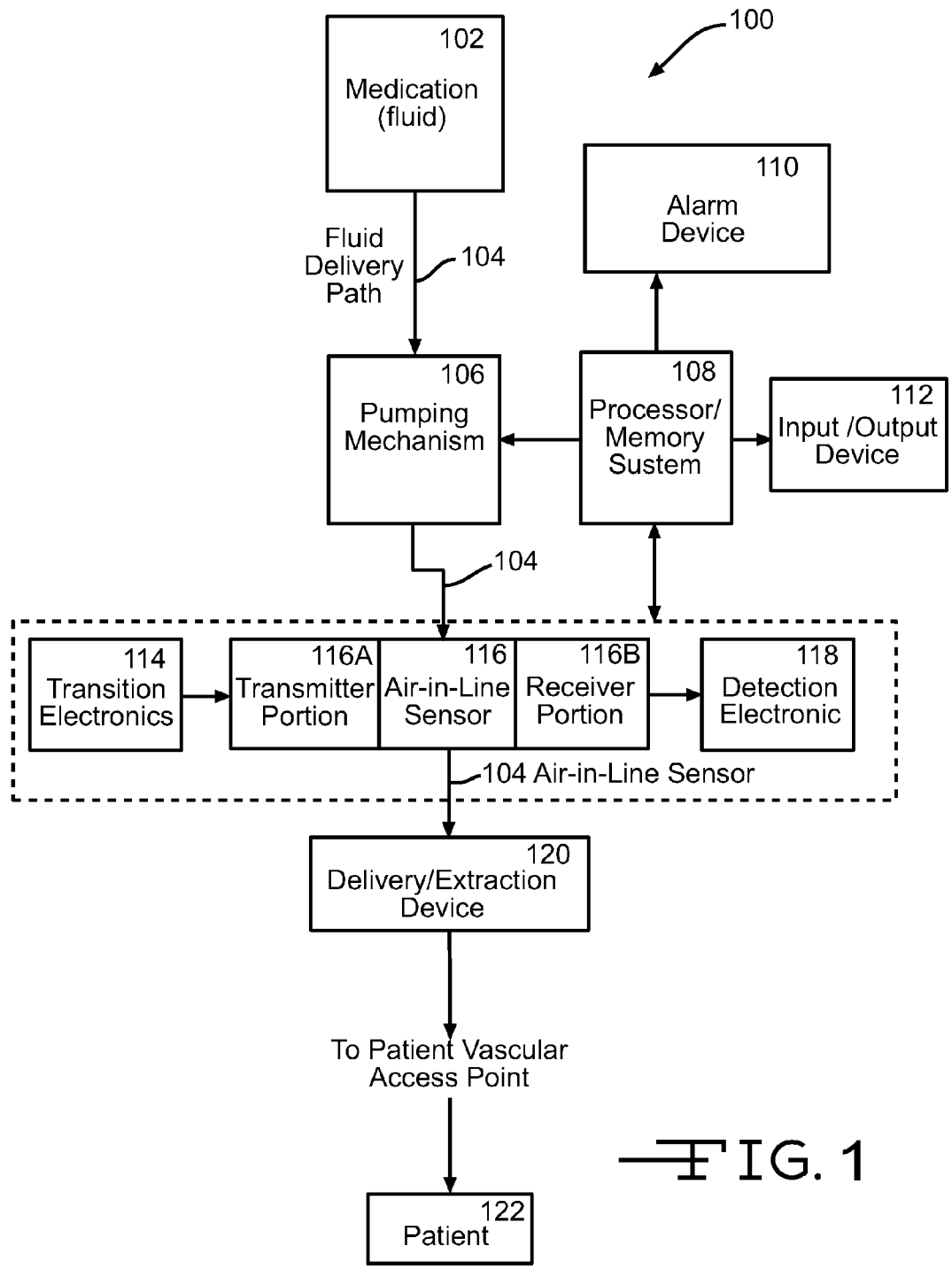
FIG. 1 illustrates a block diagram of a drug delivery infusion system under one embodiment of the disclosure.

FIG. 1 illustrates a block diagram of a drug delivery infusion system 100 under one embodiment of the disclosure. The drug delivery infusion system 100 comprises: a fluid supply container 102; a fluid delivery line 104; a pumping device 106; a processing device 108; an alarm device 110; an input/output device 112; an electronic transmitting device 114; an air-in-line sensor 116; a electronic detection device 118; and a delivery/extraction device 120. The drug delivery infusion system 100 may comprise a drug delivery infusion system such as the PLUM A+™, GEMSTAR™, SYMBIQ™ or other type of drug delivery infusion system. The fluid supply container 102 comprises a container for delivering fluid such as IV fluid or a drug to the patient 122. The fluid delivery line 104 comprises one or more tubes, connected between the fluid supply container 102, the pumping device 106, the air-in-line sensor 116, and the delivery/extraction device 120, for transporting fluid from the fluid supply container 102, through the pumping device 106, through the air-in-line sensor 116, through the delivery/extraction device 120 to the patient 122. The fluid delivery line 104 may also be used to transport blood, extracted from the patient 122 using the delivery/extraction device 120, through the air-in-line sensor 116 as a result of a pumping action of the pumping device 106. The pumping device 106 comprises a pump for pumping fluid from the supply container 102 or for pumping blood from the patient 122.

The pumping device 106 may comprise a plunger based pump, a peristaltic pump, or another type of pump. The processing device 108 comprises a processor for processing information received from the air-in-line sensor 116 and for executing a software algorithm to determine if air, liquid, or a struck-fluid droplet is located in the fluid delivery line 104 at the location of the air-in-line sensor 116. The processing device 108 includes a memory and a clock. The alarm device 110 comprises an alarm, triggered by the processing device 108, for notifying the clinician as to the presence of excessive air or a stuck-fluid droplet in the fluid delivery line 104 at the location of the air-in-line sensor 116, and for stopping the pumping device 106 prior to an air embolism being delivered through the fluid delivery line 104 and the delivery/extraction device 120 to the patient 122. The input/output device 112 comprises a device which allows a clinician to input information, such as a user-inputted medication infusion program, to the processing device 108, and which also outputs information to the clinician.

The electronic transmitting device 114 comprises electronic circuitry, connected to the air-in-line sensor 116, which transmits a signal from a transmitter portion 116A of the air-in-line sensor 116, through fluid delivery line 104, to a receiver portion 116B of the air-in-line sensor 116 connected to the electronic detection device 118. The air-in-line sensor 116 is connected to the fluid delivery line 104 distal of the pumping device 106. In other embodiments, the air-in-line sensor 116 may be located proximal to the pumping device 106 or may be located in both proximal and distal positions. The transmitter and receiver portions 116A and 116B of the air-in-line sensor 116 sense the presence of air or fluid within the fluid delivery line 104. The transmitter and receiver portions 116A and 116B of the air-in-line sensor 116 comprise a transducer such as an ultrasonic sensor, an acoustic sensor, an optical sensor, or another type of sensor. The electronic detection device 118 comprises electronic circuitry, connected to the receiver portion 116B of the air-in-line sensor 116, for receiving the signal transmitted from the electronic transmitting device 114, through the transmitter portion 116A of the air-in-line sensor 116, through the fluid delivery line 104, to the receiver portion 116B of the air-in-line sensor 116, to the electronic detection device 118. Alternate arrangements of the sensor transmitter and receiver are possible and include both side-by-side arrangements and the use of a single transducer to both transmit and receive a reflected signal. The delivery/extraction device 120 comprises a patient vascular access point device for delivering fluid from the fluid supply container 102 to the patient 122, or for extracting blood from the patient 122. The delivery/extraction device 120 may comprise a needle, a catheter, or another type of delivery/extraction device.

Figure 2:
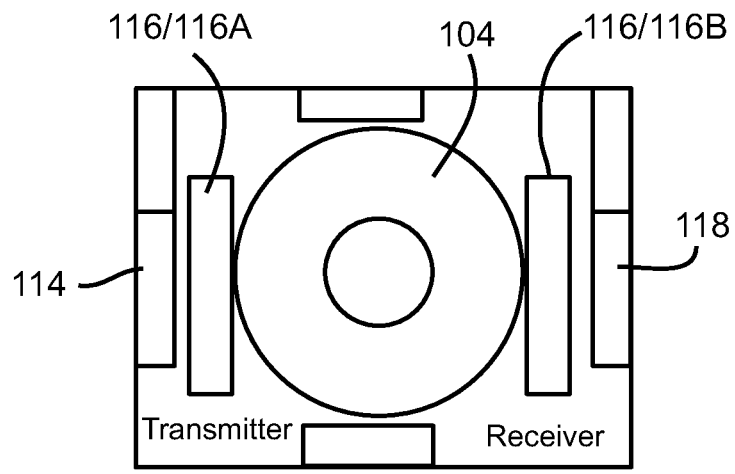
FIG. 2 illustrates a cross-section through one embodiment of a segment of a fluid delivery line coupled to an air-in-line sensor.

FIG. 2 illustrates a cross-section through one embodiment of a segment of fluid delivery line 104 coupled to the electronic transmitting device 114, the transmitter portion 116A of the air-in-line sensor 116, the receiver portion 116B of the air-in-line sensor 116, and the electronic detection device 118. The transmitter and receiver portions 116A and 116B of the air-in-line sensor 116 comprises piezoelectric crystals compressed against each side of the fluid delivery line 104 creating more surface area for uniform acoustic coupling and better signal to noise ratio. This arrangement of the transmitter and receiver portions 116A and 116B of the air-in-line sensor 116 enables the transmission and detection of an ultrasonic signal through a target volume of the infusion line fluid delivery line 104. The electronic transmitting device 114 generates a nominal 5.25 MHz ultrasonic signal directed from the transmitter 116A portion of the air-in-line sensor 116, through the fluid delivery line 104, to the receiver portion 116B of the air-in-line sensor 116 connected to the electronic detection device 118. When liquid is present in the fluid delivery line 104 at the position of the air-in-line sensor 116, the receiver portion 116B of the air-in-line sensor 116 and the electronic detection device 118 generate a larger electrical signal than when air is present at the same position. Because of an inversion in the electronics of the electronic detection device 118, the software of the processing device 108 will receive a low signal when liquid is present at the location of the air-in-line sensor 116, and a high signal when air is present at the location of the air-in-line sensor 116. When a cassette is loaded into the pumping device 106, the segment of the fluid delivery line 104 distal to the cassette is clamped into place in front of the air-in-line sensor 116. This enables reliable and repeatable sensor performance over multiple cassettes.

Figure 3:
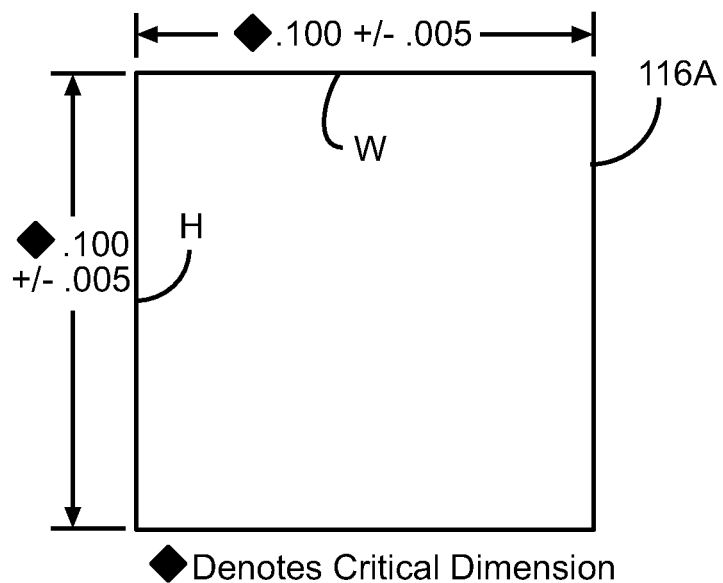
FIG. 3 illustrates a top view through one embodiment of piezoelectric crystals of an air-in-line sensor.

FIG. 3 illustrates a top view through one embodiment of the piezoelectric crystals of the transmitter portion 116A of the air-in-line sensor 116. As shown, the height H of the air-in-line sensor 116 comprises 0.100 inches and the width W of the air-in-line sensor 116 comprises 0.100 inches. The dimensions of the receiver portion 116B of the air-in-line sensor 116 are identical to the transmitter portion 116A of the air-in-line sensor 116. In other embodiments, the dimensions of the transmitter and receiver portions 116A and 116B of the air-in-line sensor 116 may vary.

The ability of the ultrasonic signal to propagate from the transmitter portion 116A to the receiver portion 116B of the air-in-line sensor 116 is governed by the acoustic impedance of the materials. The matching layers of the transducers of the transmitter and receiver portions 116A and 116B are designed to control the amplitude of the reflections at the piezo-matching layer and matching layer-fluid delivery line interfaces. The other significant component of the signal path is the liquid or air inside the fluid delivery line 104. The acoustic impedances (Za) @ 20° C. of interest are as follows: water=$1.5 \times 10^6$ kg/(m² s); PVC=$3.3 \times 10^6$ kg/(m² s); and air=413.2 kg/(m² s). Reflections of the ultrasonic signal occur at material boundaries and are governed by the differences in acoustic impedance. The reflection coefficient (RC) is defined as: $RC=(Za-Za1)/(Za+Za1)$. A high RC indicates that the signal will not pass through the boundary. For the PVC to water interface, the RC=0.375 which indicates that a majority of the signal will pass through the interface. For the PVC to air interface, the RC=0.999 which indicates that none of the signal will pass through the interface.

The electronic detection device 118A converts the signal received by the receiver portion 116B of the air-in-line sensor 116 back to an electrical signal as governed by the equation: Vout=$\lambda$ Tpiezo $\sigma$/Drvr, where Vout=the electrical signal received by the receiver portion 116B of the air-in-line sensor; $\lambda$=the strain on the piezo crystal due to the ultrasonic wave; $\sigma$=the stress on the piezo crystal due to the ultrasonic wave; Tpiezo=the thickness of the piezo crystal; Drvr=the mechanical displacement of the piezo by the ultrasonic crystal. Thus, when fluid is in the fluid delivery line 104, the receiver portion 116B of the air-in-line sensor 116 is able to collect a large amount of ultrasonic energy since fluid is a better conductor then air. This appears as a low voltage at the ND converter of the electronic detection device 118 because the signal received by the receiver portion 116B of the air-in-line sensor 116 is inverted electrically. The position of the droplet inside the fluid delivery line 104 relative to the transmitter and receiver portions 116A and 116B of the air-in-line sensor 116 also influences the amount of energy the receiver portion 116B of the air-in-line sensor detects. When air is in the fluid delivery line 104, the receiver portion 116B of the air-in-line sensor 116 collects little energy.

Figure 4:
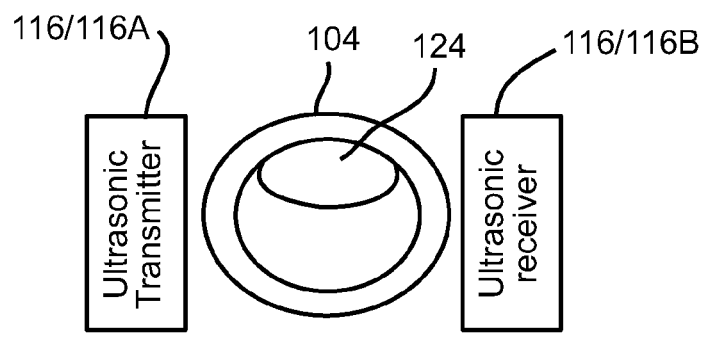
FIG. 4 illustrates a cross-section view through one embodiment of a segment of fluid delivery line having a fluid droplet stuck in the fluid delivery line at an air-in-line sensor.

FIG. 4 illustrates a cross-section view through one embodiment of a segment of fluid delivery line 104 with a stationary fluid droplet 124 in the fluid delivery line 104 between the transmitter portion 116A of the air-in-line sensor 116 and the receiver portion 116B of the air-in-line sensor 116. When a fluid droplet 124 is stationary in the fluid delivery line 104 by the air-in-line sensor 116, the fluid droplet 124 provides a better path than air alone and the receiver portion 116B of the air-in-line sensor 116 collects more energy than if just air was present at the air-in-line sensor 116. The formation of a stuck (or stationary) droplet of fluid 124 occurs all along the fluid delivery line segment 104 when there is a transition from fluid delivery to air delivery. If the stuck droplet 124 forms between the transmitter and receiver portions 116A and 116B of the air-in-line sensor 116, as shown in FIG. 4, an acoustic short circuit results leading to a decrease in the digitized air sensor voltage (analog-to-digital counts or "ADC") received and inverted by the electronic detection device 118 of FIGS. 1 and 2. If the energy collected from the stuck droplet 124 was more than the air/liquid threshold programmed in the software of most current air-detection systems, most current air detection systems would indicate that they had detected fluid when in fact air was present in the fluid delivery line 104 at the air-in-line sensor 116.

The drug delivery infusion system 100 of the instant disclosure overcomes this issue by utilizing an algorithm, programmed in the processing device 108 of FIG. 1, that detects a pattern associated with the stuck droplet 124 of FIG. 4 indicating the presence of the stuck droplet 124 at the air-in-line sensor 116. The processing device 108 of FIG. 1 includes software components that receive the digitized air-in-line signal received by the receiver portion 116B of the air-in-line sensor 116 though the electronic detection device 118. The processing device 108 processes the received digitized air-in-line signal, analyzes the processed sensor signal, and generates an alarm, using the alarm device 110 of FIG. 1, when the software indicates that air over the air threshold is present including in the situation of a stuck droplet 124 located at the air-in-line sensor 116 as shown in FIG. 4.

Figure 5:
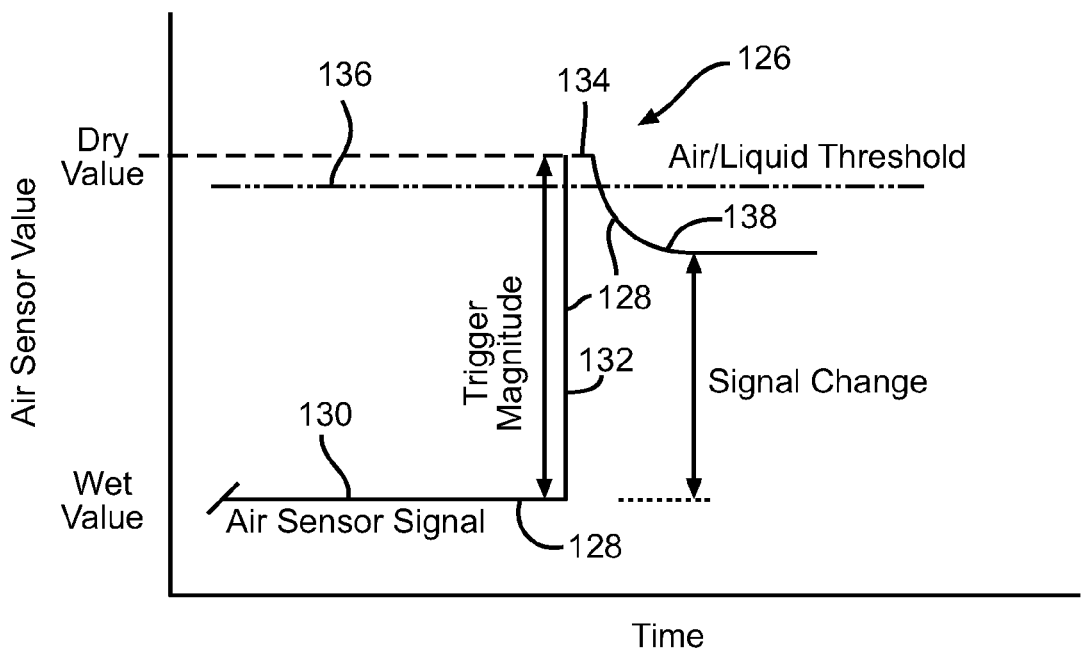
FIG. 5 is a graph plotting air-sensor ADC values versus time for one embodiment of an exemplary signal pattern associated with the formation of a stuck fluid droplet stuck over an air-in-line sensor within a fluid delivery line.

FIG. 5 is a graph 126 plotting air-sensor ADC values versus time illustrating an exemplary signal pattern 128 which was discovered is associated with the formation of a stuck fluid droplet 124 which is stuck (stationary) at the location of an air-in-line sensor 116 within fluid delivery line 104 as shown in FIG. 4. As shown, initially the air sensor ADC value is at liquid level 130 with a low air sensor ADC value. As fluid delivery comes to an end at point 132, there is an abrupt discontinuity involving a jump from the liquid ADC level 132 to ADC level 134 above the known air/liquid threshold boundary 136 and a period of observed air delivery at level 134 ensues in which the sensed ADC level remains above the Air/Liquid Threshold. If no stuck droplet 124 (shown in FIG. 4) is formed, the ADS signal remains at level 134 above the air/liquid threshold boundary 136 and the processing device 108 of FIG. 1 triggers the alarm device 110 and suspends the pumping device 106 due to the presence of air in the system. However, when a stationary liquid droplet 124 (shown in FIG. 4) forms, the ADC signal is attenuated and drops from level 134 below the air/liquid threshold boundary 136 to level 138 where it remains semi-stationary. In this situation, although air continues to pass by the sensor and down the fluid delivery line, most current air detection systems would give an erroneous "liquid" designation due to the attenuated ADC signal. However, in this situation, the drug delivery infusion system 100 of FIG. 1 of the instant disclosure detects a pattern that appears due to the attenuated ADC signal and distinguishes the presence of the stuck droplet 124 at the air-in-line sensor 116 as shown in FIG. 4.

Figure 6:
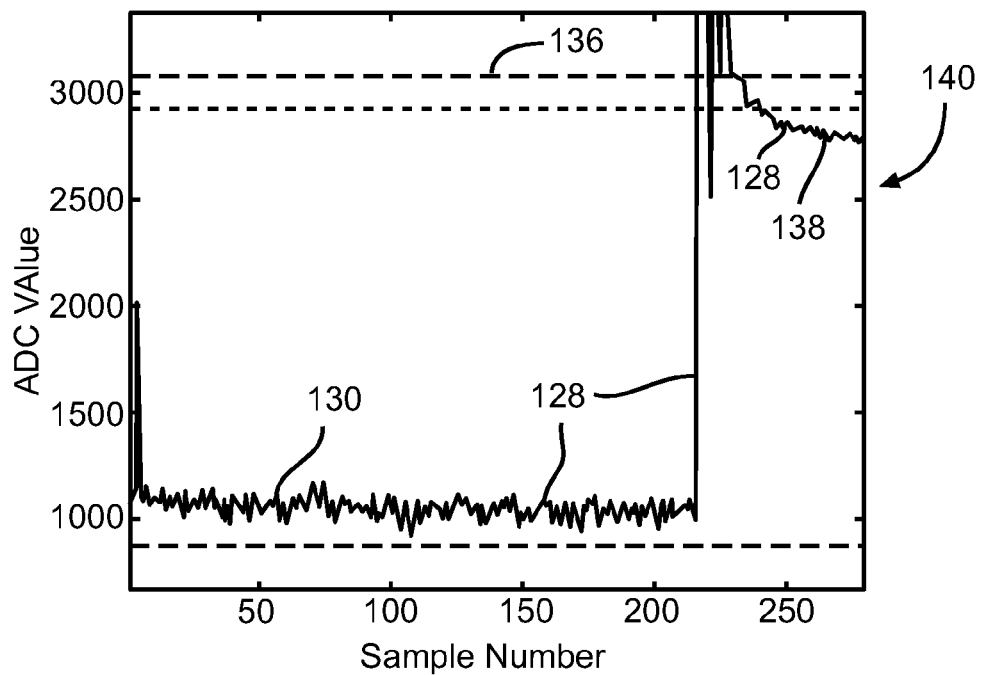
FIG. 6 is a graph plotting air-sensor ADC values versus sample numbers for another embodiment of a laboratory-observed signal pattern associated with stuck fluid droplets stuck over an air-in-line sensor within a fluid delivery line.
Figure 7:
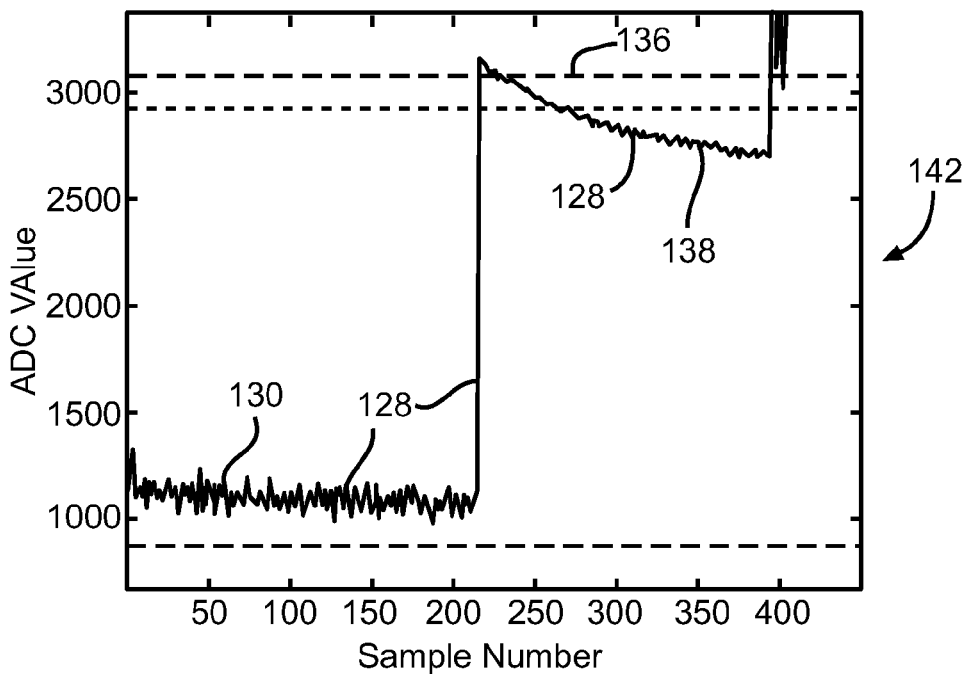
FIG. 7 is a graph plotting air-sensor ADC values versus sample numbers for still another embodiment of a laboratory-observed signal pattern associated with stuck fluid droplets stuck over an air-in-line sensor within a fluid delivery line.
Figure 8:
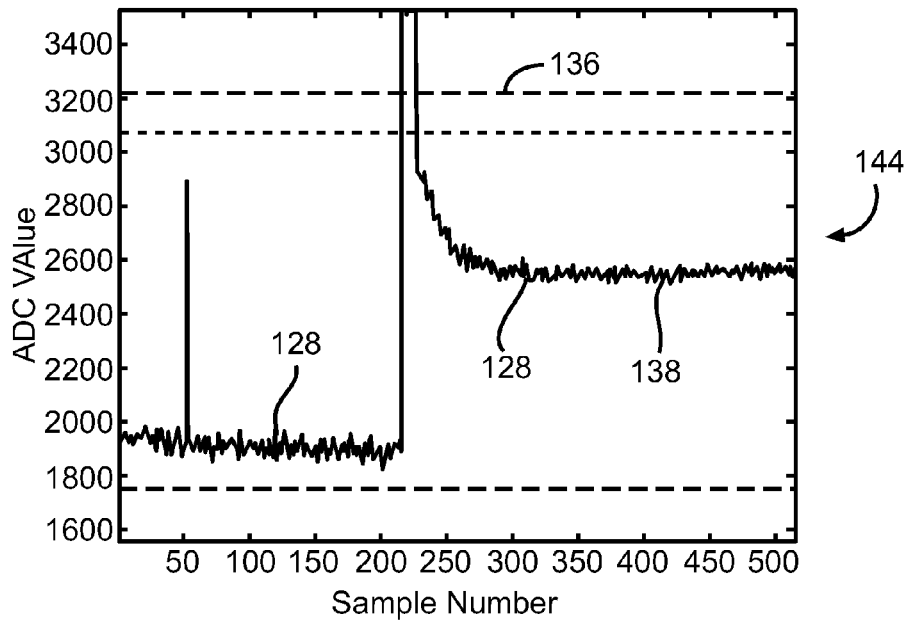
FIG. 8 is a graph plotting air-sensor ADC values versus sample numbers for yet another embodiment of a laboratory-observed signal pattern associated with stuck fluid droplets stuck over an air-in-line sensor within a fluid delivery line.

FIGS. 6-8 depict graphs 140, 142, and 144 plotting air-sensor ADC values versus sample numbers for different embodiments of separate laboratory-observed signal patterns 128 associated with stuck fluid droplets 124 which were stuck at the location of an air-in-line sensor 116 within fluid delivery line 104 as shown in FIG. 4. While stuck fluid droplets 124 result in unique ADC patterns 128, the time series of these signals have common features or characteristics that distinguish them from typical ADC patterns allowing the identification of a stuck fluid droplet 124 based on the ADC pattern.

First, it has been discovered that stuck fluid droplets 124 result in the ADC jumping from a liquid level 130 that is below the Air/Liquid Threshold to a level that is close to or above the air/liquid threshold boundary 136. This is referred to as the "triggering event". In most cases, the triggering event causes the ADC value to jump above the air/liquid threshold boundary 136, also referred to as the "primary" threshold. Due to the liquid/air transition, there is necessarily a jump discontinuity and a leading edge in the ADC signal. Second, it has been discovered that for stuck fluid droplets 124, after a brief period above or near the primary threshold 136, the ADC value falls to a level that is between the primary threshold 136 and the previously observed wet level 130. Third, it has been discovered that for struck fluid droplets 124, the ADC signal level following the stuck droplet formation is stable in one of the following two ways: (1) the ADC value 138 gradually changes with time, as illustrated in FIGS. 6 and 7, representing a stuck droplet 124 formed in front of the air-in-line sensor 116 (as shown in FIG. 4) which is moving slowly leading to a gradually increasing or decreasing ADC value; or (2) the ADC value 138 stays stationary without any unusual jump in ADC values, as illustrated in FIG. 8, representing a static droplet 124 stuck in front of the air-in-line sensor 116 (as shown in FIG. 4) forming a short circuit between the transmitter portion 116A and receiver portion 116B of the air-in-line sensor 116.

In both situations, the ADC value is changing but the post-droplet formation segment of the signal is piece-wise continuous with a low variance through time. It has been discovered that dramatic changes in the ADC value do not take place when a stuck droplet 124 occurs at the air-in-line sensor 116. These characteristics represent a three phase system which forms a pattern over time. It is possible to add additional phase granularity. For example, pre-trigger, the signal could be further classified as having one of the following characteristics: constant flow without air bubbles; constant flow with small moving bubbles; constant flow with static bubbles at the air-line-sensor with small moving bubbles; constant flow with relatively large air bubbles; and mixtures of varied concentration containing both air and fluid (froth). Similarly, after the trigger event the signal can be further characterized according to the mixture of fluid and air. However, the three identified phases enable the fundamental classification of stuck droplet formation via the minimal set of observational data. The air-in-line stuck droplet software module of the instant disclosure is based upon this discovery, which connects the physical formation of a liquid droplet to the temporal air sensor signal through time.

The stuck droplet algorithm of the instant disclosure was designed to detect air in the presence of a stagnant or relatively stationary fluid droplet(s) 124 at the location of the air-in-line sensor 116, disposed between the transmitting portion 116A and receiving portion 116B of the air-in-line sensor 116 (as shown in FIG. 4), without increasing nuisance alarms.

No changes are necessary to current infusion systems' existing air bubble detection algorithms, or cumulative air detection algorithms, in order to implement the stuck droplet system and method of the instant disclosure in order to identify stuck fluid droplet(s) 124. The stuck droplet algorithm of the instant disclosure is configured to use pattern recognition to detect the droplet formation process rather than detecting the actual stuck droplet 124 itself. The droplet formation process is a dynamic event which occurs all along the fluid delivery line 104 as the liquid front recedes. However, since the stuck droplet 124 has to form in front of the air-in-line sensor 116 for it to cause air detection failure, the event is observable by the air-in-line sensor 116. Therefore, by analyzing the signal pattern from the air-in-line sensor 116, the stuck droplet 124 can be reliably detected.

The algorithm of the instant disclosure has several key elements that distinguish it from prior approaches. First, the algorithm acts upon a multi-state ADC signal pattern that is consistent with the formation of a stuck droplet 124 in front of the air-in-line sensor 116. Because the stuck droplet 124 forms an acoustic short-circuit, the air-in-line sensor signal associated with a stuck droplet 124 is indistinguishable from a fluid level. Therefore, detection of the presence of a stuck droplet 124 is only possible through the temporal formation sequence. Second, the algorithm has multiple states. Transitions between states are governed by specific rules. Third, the algorithm is designed to reject false positives. Fourth, the algorithm is adaptive and includes a method for automatically measuring the dynamic range of the air sensor system and thereby adjusting various parameters (thresholds).

Figure 9:
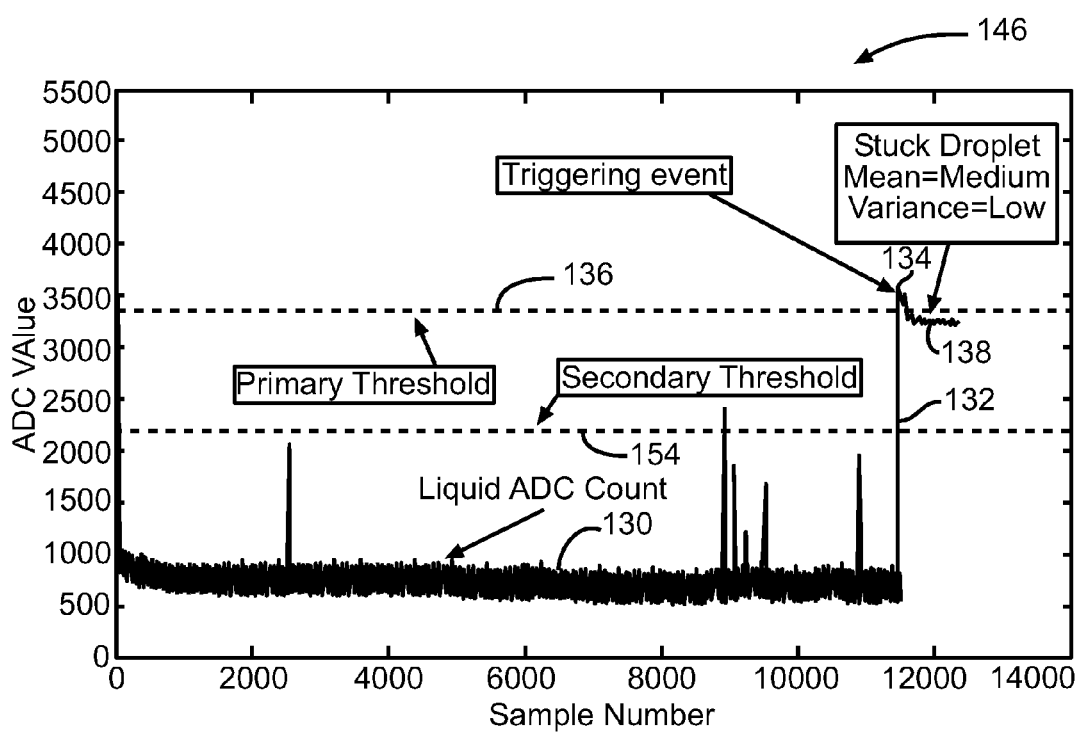
FIG. 9 is a graph plotting air-sensor ADC values versus sample numbers for still another embodiment of a stuck-fluid droplet stuck over an air-in-line sensor within a fluid delivery line.

FIG. 9 illustrates another embodiment of a graph 146 plotting air-sensor ADC values versus sample numbers for an exemplary stuck-fluid droplet 124 stuck at the location of an air-in-line sensor 116 within fluid delivery line 104 as shown in FIG. 4. At the onset of liquid infusion past the air-in-line sensor 116, the sensor ADC reading is at level 130 below the primary threshold 136 that defines the air/fluid boundary. Above the primary threshold 136 the signal is interpreted as air but below the primary threshold 136 the signal represents fluid. In the example, fluid is detected until approximately sample 11,800. An event is detected at point 132 as a result of a sudden increase in the signal level. In addition to the large increase in the ADC value, the signal rises above the primary threshold 136 to level 134. Either of these factors may produce a triggering event leading to a change in the detection algorithm state.

After the triggering event, the ADC signal remains close to or above the primary threshold 136 for a period of time. Subsequently, as a result of the formation of a stuck fluid droplet 124, the signal drops below the primary threshold 136 to level 138. This leads to another change in state as the algorithm begins to evaluate the stability of the signal. If the signal varies substantially or drops back down to or below the previously observed fluid level 130, or, if the signal drops below a secondary threshold 154, then the algorithm resets and begins to again look for another triggering event. In these cases, the triggering event resulted from an air bubble or small slug of air and not a fluid to air transition. However, if the signal is stable, then the algorithm enters a count state and begins to accumulate an "air volume" estimate. If the counter exceeds a pre-set volume, then an alarm occurs.

The stability of the signal is determined on the basis of the variability of the signal through time, in one example the variability is defined as the variance through time. However, it could also be estimated using the observed entropy, the spectral variation, the error in the fit, or other time series (statistical) or model based approaches. During the count sequence, either the stuck droplet could clear, resulting in a signal above the primary threshold 136, or fluid could again be delivered, resulting in a signal below the secondary threshold 154. In the former case the counter is reset and is discontinued until the signal again falls below the primary threshold 136. In the latter case, the state changes back to monitoring.

Fundamentally, detection of the stuck droplet formation event involves a pattern, defined herein as a definite sequence of bounded signal levels. Each mechanism is calibrated with micro bore and macro bore wet calibration sets. The dynamic wet value is initialized in the initialization state to the micro bore wet calibration value. During an infusion, if the average ADC value, $\bar{x}(k)$, is lower than the dynamic wet value, the dynamic wet value is updated to this lower value.

Figure 10:
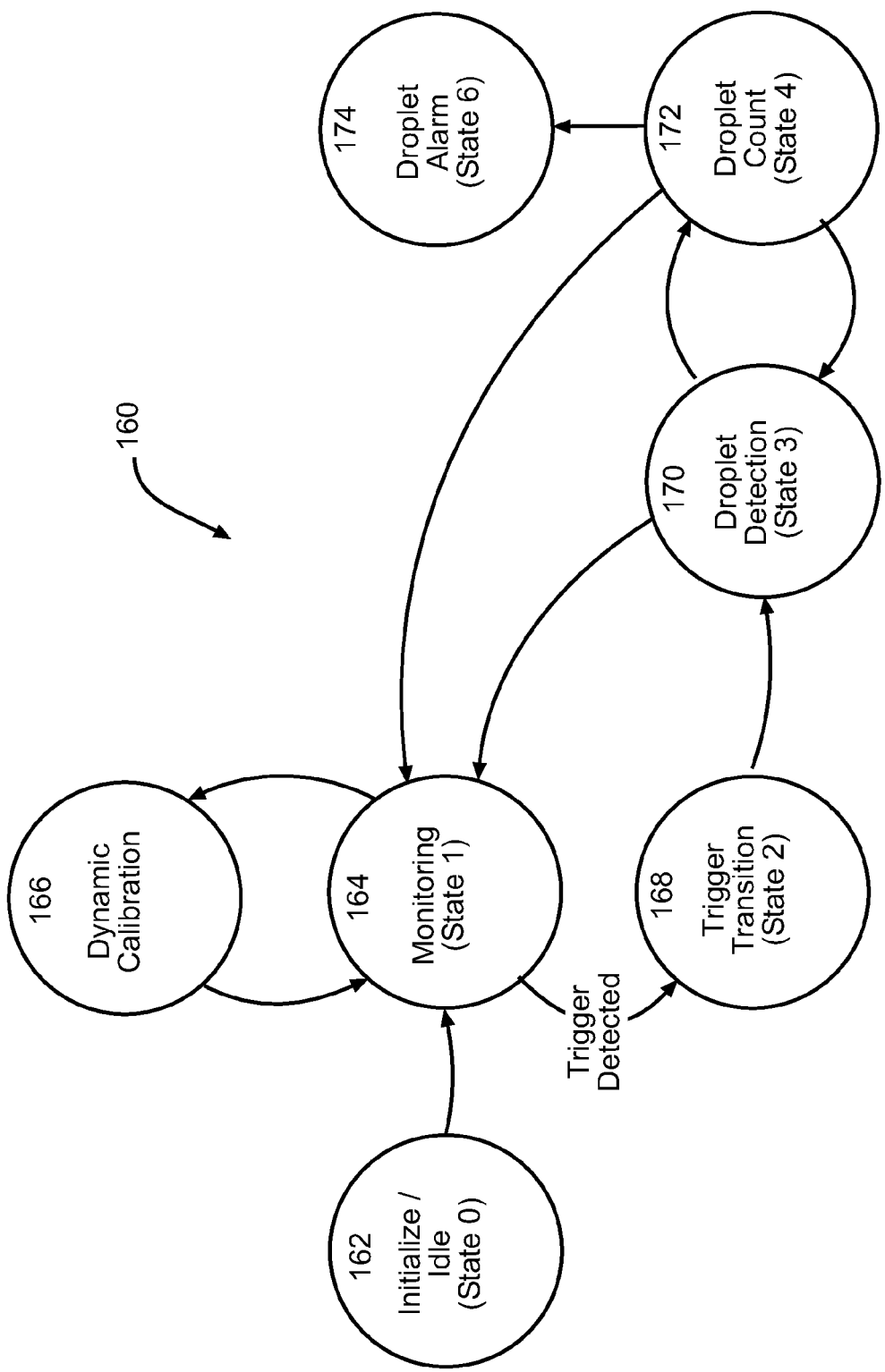
FIG. 10 is a flowchart illustrating one embodiment of a multi-state air-in-line detection method for detecting a stuck fluid droplet in a fluid delivery line.

FIG. 10 is a flowchart illustrating one embodiment of a multi-state air-in-line detection method 160 for detecting a stuck fluid droplet in fluid delivery line 104. The method 160 may be implemented using the drug delivery infusion system 100 of FIG. 1. The method 160 includes an initialization/idle state 162, a monitoring state 164, a dynamic calibration state 166, a trigger transition state 168, a droplet detection state 170, a droplet count state 172, and a droplet alarm state 174.

Figure 11:
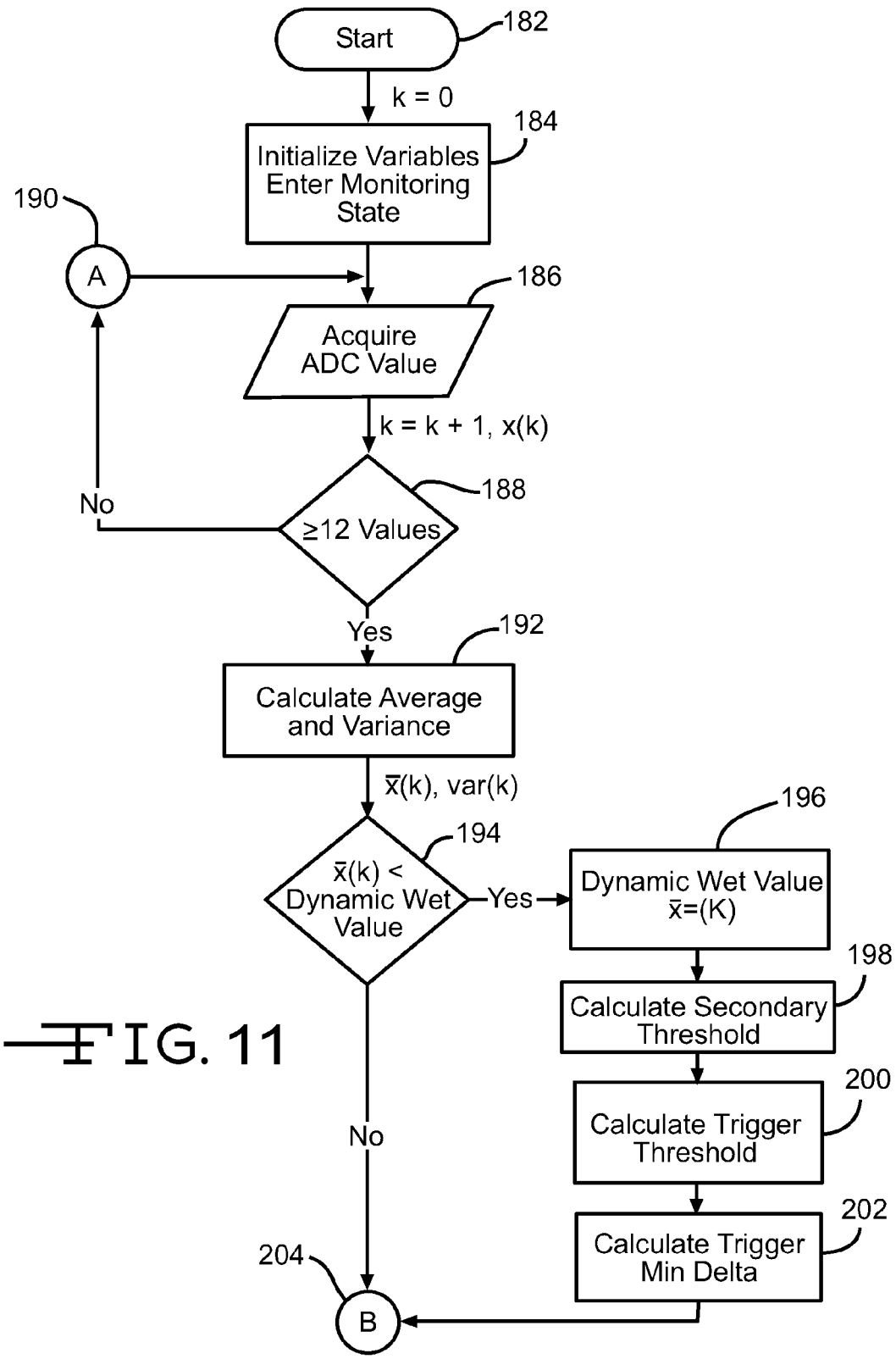
FIG. 11 is a flowchart illustrating initialization steps, monitoring steps, and dynamic calibration steps for one embodiment of a method for detecting a stuck fluid droplet in a fluid delivery line.
Figure 12:
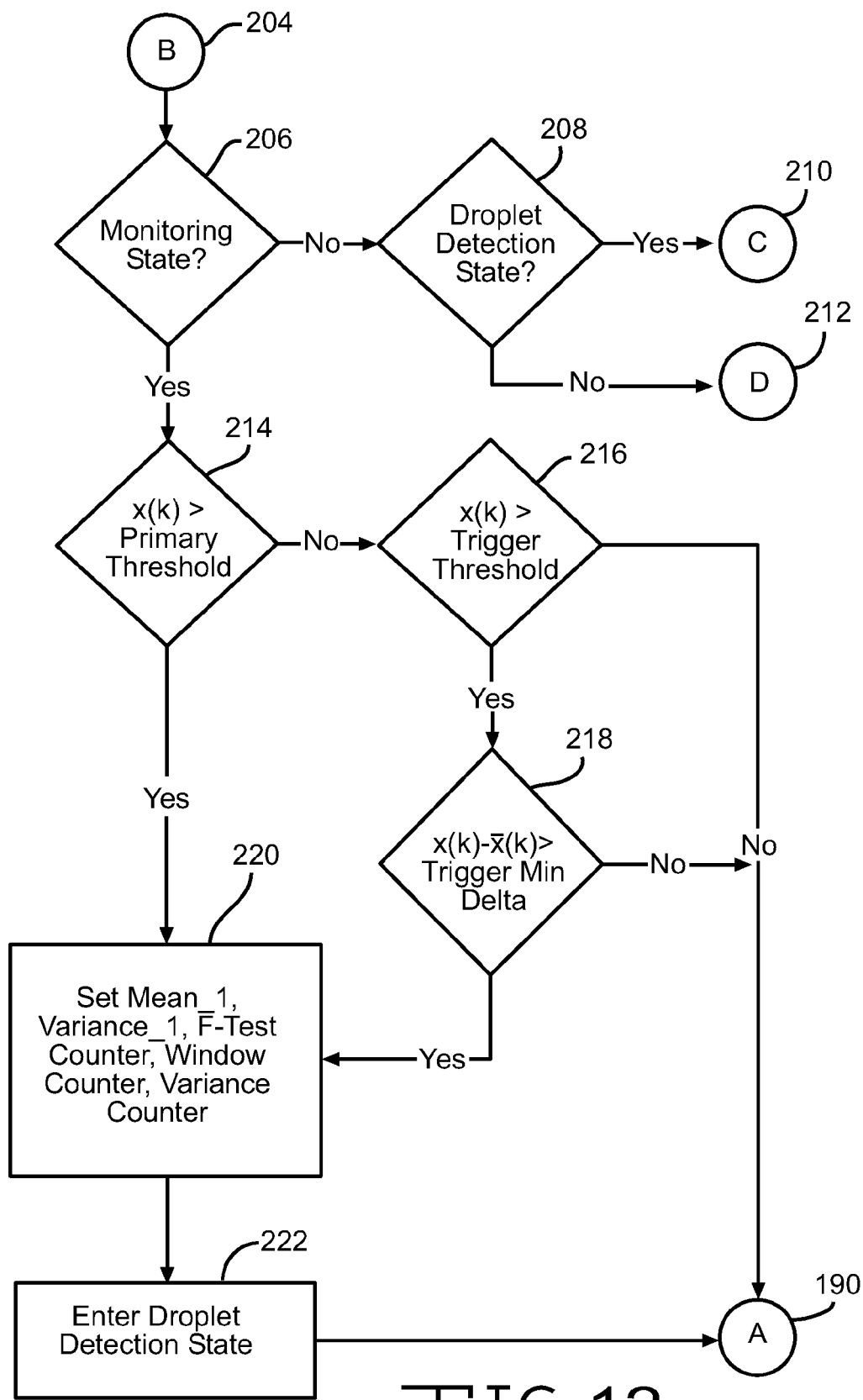
FIG. 12 is a flowchart illustrating trigger transition steps for one embodiment of a method for detecting a stuck fluid droplet in a fluid delivery line.
Figure 13:
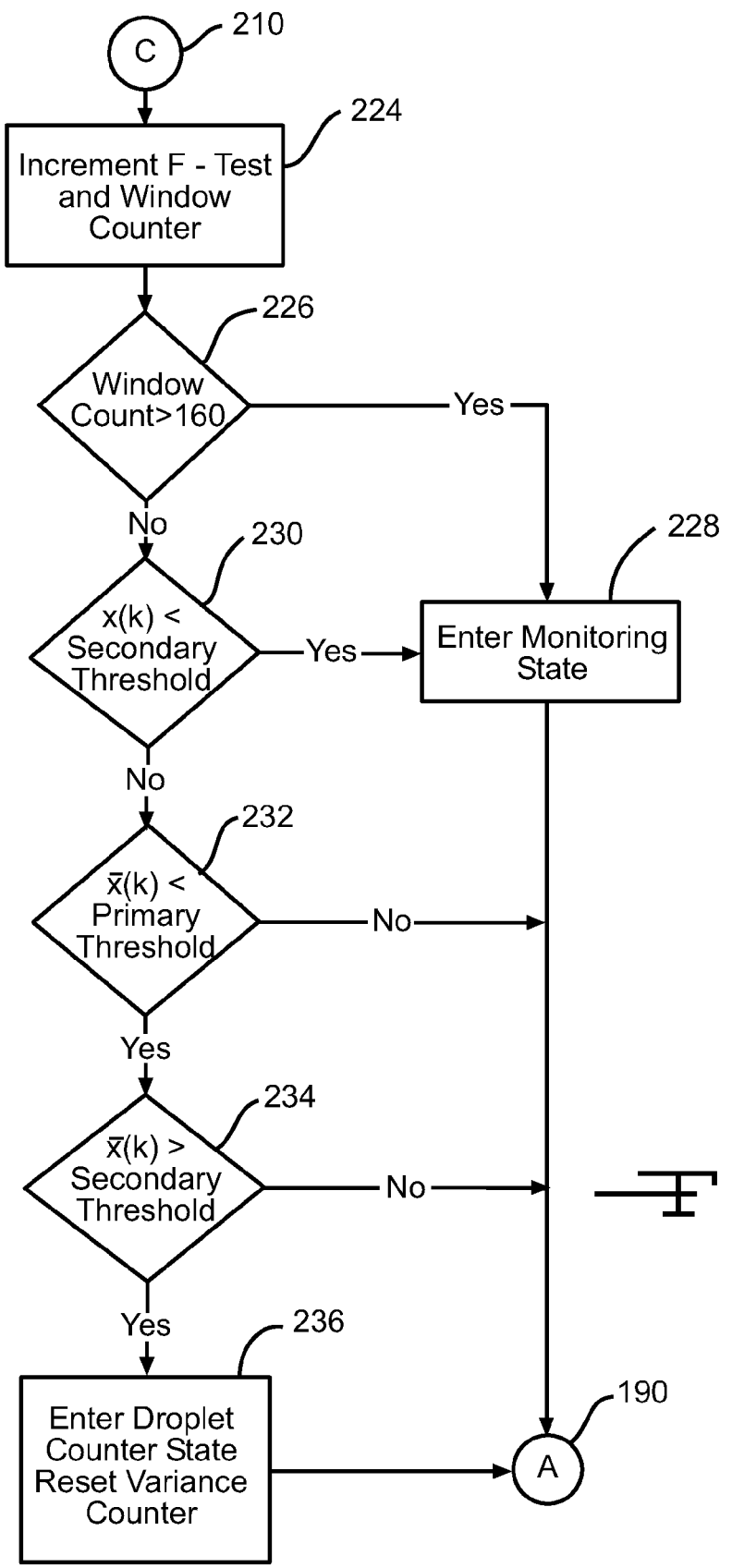
FIG. 13 is a flowchart illustrating droplet detection steps for one embodiment of a method for detecting a stuck fluid droplet in a fluid delivery line.
Figure 14:
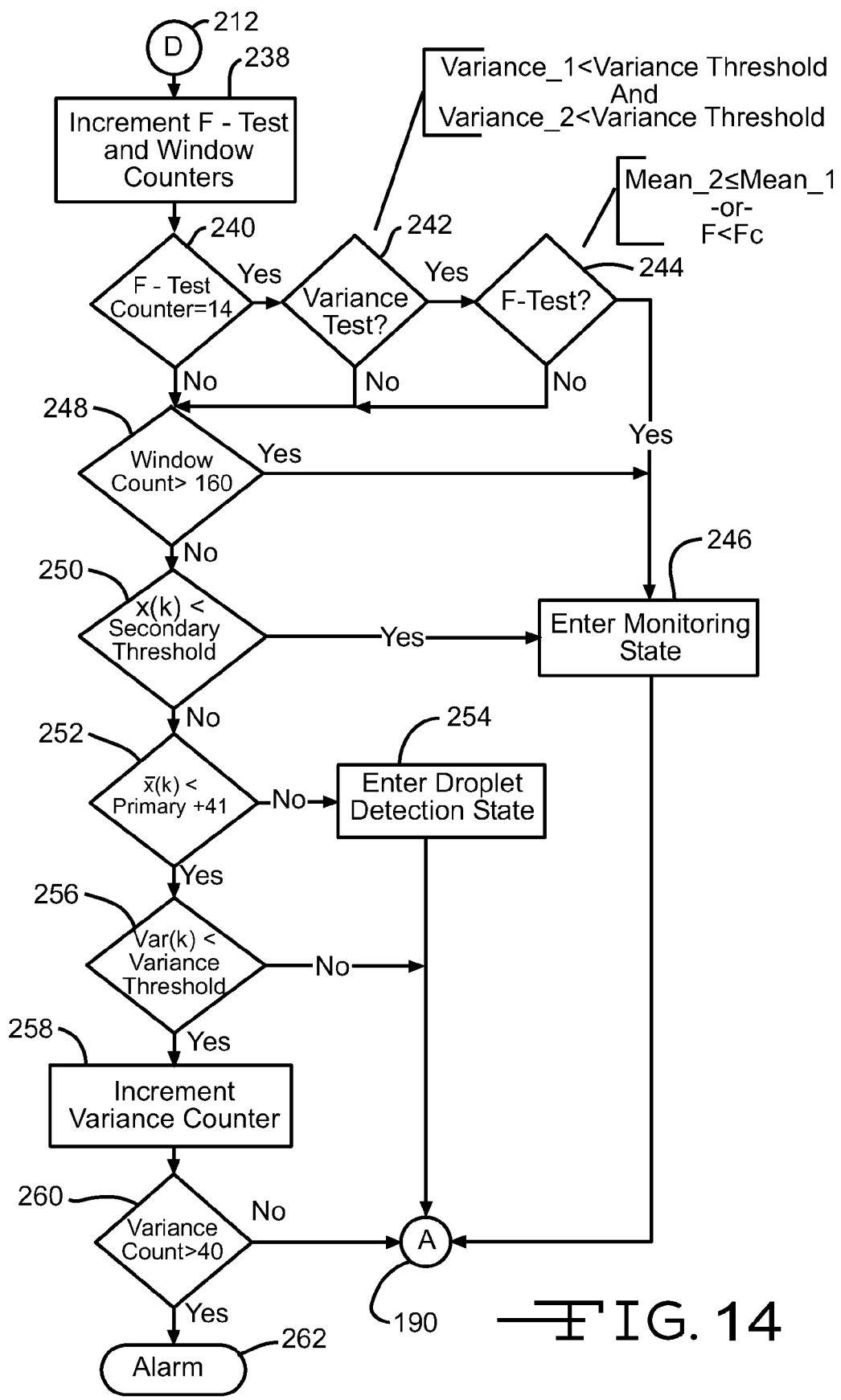
FIG. 14 is a flowchart illustrating droplet count steps and droplet alarm steps for one embodiment of a method for detecting a stuck fluid droplet in a fluid delivery line.

FIGS. 11-14 illustrate one embodiment of a continuous flowchart 180 implementing an algorithm which may be followed to detect a stuck fluid droplet 124 in fluid delivery line 104 as shown in FIG. 4. FIGS. 11-14 may be implemented using the drug delivery infusion system 100 of FIG. 1. FIG. 11 is a flowchart illustrating initialization steps, monitoring steps, and dynamic calibration steps for one embodiment of a method for detecting a stuck fluid droplet in a fluid delivery line. FIG. 12 is a flowchart illustrating trigger transition steps for one embodiment of a method for detecting a stuck fluid droplet in a fluid delivery line. FIG. 13 is a flowchart illustrating droplet detection steps for one embodiment of a method for detecting a stuck fluid droplet in a fluid delivery line. FIG. 14 is a flowchart illustrating droplet count steps and droplet alarm steps for one embodiment of a method for detecting a stuck fluid droplet in a fluid delivery line.

As shown in FIG. 11, the initialization or idle state occurs during steps 182-184 prior to the state of a medication infusion. In step 182, the method starts. After step 182, in step 184 all internal variables are re-set and the wet and dry calibration levels are set according to factory calibration procedures. During step 184, the following variables are set: (1) the 'dry value' variable is set to the ADC level set during initialization to the factory calibrated value for 'air'; (2) the 'wet value' variable is set to the ADC level set during initialization to the factory calibrated value for 'fluid'; (3) the 'primary threshold' variable (also referred to as the air/water threshold) is calculated as being primary threshold=dry value−150 ADC; (4) the 'dynamic wet value' variable is initially set to the 'wet value' variable and adaptively updates during the method to take into account variations in the observed 'wet value' variable; (5) the 'secondary threshold' variable comprises the minimum observed ADC level to remain in the droplet search or droplet count states and is calculated as being secondary threshold=0.5*(primary threshold−dynamic wet value)+dynamic wet value; (6) the 'trigger threshold' variable comprises the minimum ADC trigger vale calculated as trigger threshold=dry value−max (150, 0.25*(dry value−dynamic wet value)) where the max represents the maximum value of the variables 150 and 0.25*(dry value−dynamic wet value); (7) the 'trigger min delta' variable comprises the minimum ADC jump associated with the trigger threshold calculated as trigger min delta=max (150, 0.25*(dry value−dynamic wet value)) where the max represents the maximum value of the variables 150 and 0.25*(dry value−dynamic wet value); and (8) all calculated variables calculated during any of the steps of the continuous flowchart 180 are reset including counters, means, and variances. For instance, the variable 'k' representing the sample number is reset to zero.

As an example of implementing step 184 during one embodiment, assume the initial factory calibrated value for the dry value=3,169 and the initial factory calibrated value for the wet value=2,000. Applying the formulas recited above during step 184, the primary threshold=dry value−150 ADC=3,169−150=3,019. The dynamic wet value=the initial wet value=2,000. The secondary threshold=0.5*(primary threshold−dynamic wet value)+dynamic wet value=0.5*(3,019−2,000)+2,000=2,509.50. The trigger threshold=dry value−max (150, 0.25*(dry value−dynamic wet value))=3,169−max (150, 0.25*(3,169−2,000))=3,169−max (150, 292.25)=3,169−max (150, 292.25)=3,169−292.25=2,876.75. The trigger min delta=max (150, 0.25*(dry value−dynamic wet value))=max (150, 0.25*(3,169−2,000))=max (150, 292.25)=292.25.

Figure 15:
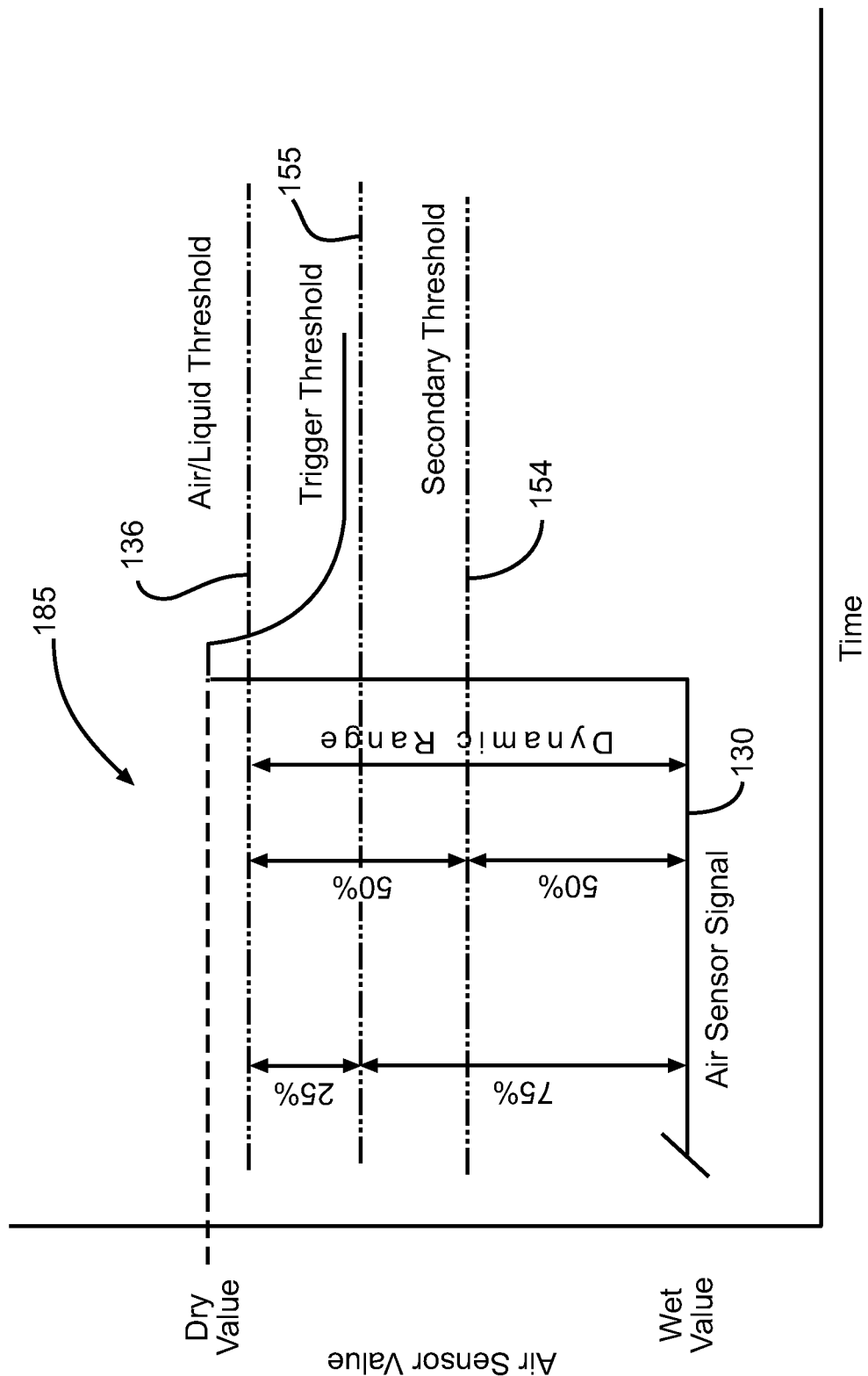
FIG. 15 is a graph plotting air-sensor ADC values versus time illustrating yet another embodiment of a laboratory-observed signal pattern associated with stuck fluid droplets stuck over an air-in-line sensor within a fluid delivery line.

FIG. 15 illustrates a graph 185 plotting air-sensor ADC values versus time for one embodiment of a typical laboratory-observed signal pattern associated with stuck fluid droplets stuck over an air-in-line sensor within a fluid delivery line. The graph 185 illustrates a pictorial definition for the wet value 130, the secondary threshold 154, the trigger threshold 155, and the primary threshold 136 as calculated during step 184 of FIG. 14 for one embodiment.

As shown in FIG. 11, the monitoring state includes steps 186-192 during a medication infusion. During the monitoring state, the ADC signal level is processed in real-time using a digital low-pass filter to attenuate noise and provide a baseline for event detection. The low-pass filter applied in one embodiment is a moving average spanning twelve samples, with each particular sample represented by k, the total number of samples represented by N=12 samples, and with the twelve samples representing 150 μL. The twelve samples define the average window which optimally reduces the noise. Each time the monitoring state is entered throughout the method, the average and variance of the air sensor measurement through time is determined based upon the twelve most recent ADC sample measurements. Consequently, a minimum of twelve ADC values must be collected prior to making these calculations.

After step 184, in step 186 the ADC value of the current sample is collected using the air-in-line sensor 116. In step 186, the sample number k being collected is determined using the formula k=k+1. For instance, when the ADC value of the first sample is collected k=k+1=0+1=1 since k is initially 0 prior to any samples being collected. The processing device 108 of FIG. 1 stores the collected ADC value for each incremental sample number as X(k) in f a buffer. After step 186, in step 188 it is determined if the ADC values of twelve or more samples have been collected by checking if k of the current sample is greater than or equal to 12. If the ADC values for less than twelve samples have been collected (k is less than 12), then the method proceeds through location step 190 back to step 186 and repeats steps 186-190 until separate ADC values have been collected for twelve or more samples until the value of k, calculated by the formula k=k+1, is greater than or equal to twelve. After collecting the ADC values for twelve or more samples, the method proceeds to step 192. In step 192, the average ADC value $\bar{x}(k)$ is determined using the formula:

$$\bar{x}(k) = \frac{1}{N} \sum_{i=k-N+1}^{k} x_i$$

where $x_i$ is the ADC reading associated with the ith sample. Similarly, in step 192, a running average estimate of the variance, Var(k), is determined using the formulas:

$$S = \sum_{i=1}^{N} x_i^2 - \frac{1}{N}\left(\sum_{i=1}^{N} x_1\right)^2$$

$$Var(k) = \frac{S}{N-1}$$

It is noted that the first average ADC value $\bar{x}(k)$ will be for k=12 after the twelfth sample, and that the first running average estimate of the variance, Var(k), will also be for k=12 after the twelfth sample.

As shown in FIG. 11, the dynamic calibration state occurs during steps 194-204. After step 192, the method proceeds to step 194. In step 194, a determination is made if the average ADC value, $\bar{x}(k)$, is less than the dynamic wet value. If the average ADC value, $\bar{x}(k)$, is determined in step 194 to not be less than the dynamic wet value, then the method proceeds through location step 204 to location step 204 of FIG. 12 and either remains in the monitoring state or enters the trigger transition state.

If the average ADC value, $\bar{x}(k)$, is determined to be less than the dynamic wet value in step 194, then the method proceeds to step 196. In step 196, the dynamic wet value is reset to equal the average ADC value $\bar{x}(k)$. This represents an adaptive increase in the dynamic range of the air sensor system due to an estimated signal level that is lower than the previous dynamic wet level. After step 196, in step 198, the secondary threshold is recalculated by using the reset dynamic wet value in the formula secondary threshold=0.5*(primary threshold−dynamic wet value)+dynamic wet value. After step 198, in step 200 the trigger threshold is recalculated by using the reset dynamic wet value in the formula trigger threshold=dry value−max (150, 0.25*(dry value−dynamic wet value)) where the max represents the maximum value of the variables 150 and 0.25*(dry value−dynamic wet value). After step 200, in step 202 the trigger min delta is recalculated by using the reset dynamic wet value in the formula trigger min delta=max (150, 0.25*(dry value−dynamic wet value)) where the max represents the maximum value of the variables 150 and 0.25*(dry value−dynamic wet value). After step 202, the method proceeds through location step 204 to location step 204 of FIG. 12 and enters the trigger transition state.

It is noted that the dynamic calibration steps 194-204 ensures robustness of the algorithm with respect to variability of the system by adapting the estimated dynamic range, and the algorithm thresholds that depend on the dynamic range, based on the actual observed ADC values. In such manner, the algorithm is automatically adaptive and provides consistent specificity and sensitivity through time despite changes in temperature, fluid viscosity, electronic drift, mechanical coupling, fluid delivery line lining, fluid delivery line bore size, fluid delivery line material, mechanic alignment, and manufacturing tolerances.

As an example of implementing steps 186-204 during one embodiment, assuming that the twelve samples collected resulted in the following ADC values: $x_1$=1,147.8; $x_2$=3,577.5; $x_3$=3,566.7; $x_4$=1,215.8; $x_5$=1,157.2; $x_6$=1,169.0; $x_7$=1,166.0; $x_8$=1,168.5; $x_9$=1,148.5; $x_{10}$=1,150.3; $x_{11}$=1,129.8; and $x_{12}$=1,193.8. Using these exemplary ADC values, in step 192 the average ADC is determined to be $\bar{x}(12)$=1,565, while the average variance is determined to be Var(12)= 8.7868e+005. In step 194, assuming that the most recently calculated dynamic wet value is 2,000, the average ADC value $\bar{x}(12)$=1,565 is determined to be less than the dynamic wet value of 2,000. As a result, in step 196, the dynamic wet value is set to $\bar{x}(12)$=1,565. In step 198, the secondary threshold is recalculated to be secondary threshold=0.5*(primary threshold−dynamic wet value)+dynamic wet value=0.5*(3,019−1,565)+1,565=2,292. In step 200, the trigger threshold is recalculated to be trigger threshold=dry value−max (150, 0.25*(dry value−dynamic wet value))=3,169−max (150, 0.25*(3,169−1,565))=3,169−max (150, 401)=3,169−401=2,768. In step 202, the trigger min delta is recalculated to be trigger min delta=max (150, 0.25*(dry value−dynamic wet value))=max (150, 0.25*(3,169−1,565))=max (150, 401)=401.

As shown in FIG. 12, the trigger transition state occurs during step 220 for only one sample. After location step 204, it is determined in step 206 if the method is in the monitoring state. If the method is determined to not be in the monitoring state in step 206, then the method proceeds to step 208. In step 208, it is determined if the method is in the droplet detection state. If it is determined in step 208 that the method is in the droplet detection state, then the method proceeds through location step 210 to location step 210 of FIG. 13. If it is determined in step 208 that the method is not in the droplet detection state, then the method proceeds through location step 212 to location step 212 of FIG. 14.

If is determined in step 206 that the method is still in the monitoring state, then the method proceeds to step 214. In step 214 it is determined if the ADC value for x(k), with x(k) being the ADC value for the current sample, is greater than the primary threshold. If the ADC value for x(k) is determined in step 214 to not be greater than the primary threshold, then the method proceeds to step 216. In step 216, it is determined if x(k) is greater than the trigger threshold. If x(k) is determined in step 216 to not be greater than the trigger threshold, then the method proceeds through location step 190 back to location step 190 of FIG. 11 and proceeds to run through the steps of FIG. 11. If x(k) is determined to be greater than the trigger threshold in step 216, then the method proceeds to step 218. In step 218, it is determined if x(k), for the current sample, minus the average ADC value $\bar{x}(k)$ is greater than trigger min delta. If it is determined in step 218 that x(k), for the current sample, minus the average ADC value $\bar{x}(k)$ is not greater than trigger min delta, then the method proceeds through location step 190 back to location step 190 of FIG. 11 and proceeds to run through the steps of FIG. 11.

If it is determined in step 218 that x(k), for the current sample, minus the average ADC value $\bar{x}(k)$ is greater than trigger min delta, then the method proceeds to step 220. This is a trigger where the air sensor signal does not rise above the primary threshold despite a large increase in the sensor ADC level. In this case, lowering the air/liquid boundary threshold from the primary threshold is not an option because this would lead to an increase in nuisance alarms. However, combining the lower trigger threshold along with the requirement of a minimum change in ADC signal, representing the trigger min delta, curtails nuisances while enabling detection.

In step 220, the following variables are set: (1) mean__1 is saved as being the average ADC value $\bar{x}(k)$ for the current triggering event sample; (2) variance__1 is saved as being the determined average variance Var(k) for the current triggering event sample; (3) the F-test-counter, representing the number of observed samples from the trigger event to the evaluation of false positives, is reset to zero; (4) the window counter, defining the maximum number of samples after the triggering event before exiting either the droplet search or the droplet count states, is reset to zero (note that the window counter is typically set to 160 ADC samples or 2 mL); and (5) the variance counter, defined as the stability interval or variance window which defines the number of samples which must remain stable prior to an alarm, is reset to zero (note that the variance counter is typically set to 40 ADC samples or 0.5 µL). After step 220, the method proceeds to step 222 and enters the droplet detection state. After step 222, the method proceeds through location step 190 back to location step 190 of FIG. 11 and proceeds to run through the steps of FIG. 11.

In one example of the trigger function under the algorithm, assume that the current state is monitoring, the ADC value for x(k) is less than the primary threshold but greater than the trigger threshold, x(k) for the current sample minus the average ADC value $\bar{x}(k)$ is greater than trigger min delta, the primary threshold=3,169, the trigger threshold=2,877, the trigger min delta=292, the average ADC value $\bar{x}(k)$=2,000, the average variance, Var(k),=1,800, and x(k)=2,900. Applying the algorithm to the example, because 2,900 is less than 3,169, and because 2,900−2,000=900 is greater than 292, then mean__1 is set to 2,000, variance__1 is set to 1,800, the F-test-counter is reset to zero, the variance counter is resent to zero, and the window counter is reset to zero. The algorithm then enters the droplet detection state and returns to location 190 of FIG. 11. However, if in the example the current state is in the droplet detection state rather than in the monitoring state, then the algorithm proceeds through location step 210 to location step 210 of FIG. 13. If in the example the current state is not in either the monitoring state or the droplet detection state, then the method proceeds through location step 212 to location step 212 of FIG. 14.

If it is determined in step 214 that the ADC value for x(k), with x(k) being the ADC value for the current sample, is greater than the primary threshold, then the method proceeds directly to step 220 and sets the variables outlined above for step 220 in which mean__1 and variance__1 are set for the current triggering event sample, and in which the F-test-counter, the window counter, and the variance counter are reset to zero. This is a trigger representing a sudden observation of air from a prior air sensor signal level consistent with fluid. After step 220, the method proceeds to step 222 and enters the droplet detection state. After step 222, the method proceeds through location step 190 back to location step 190 of FIG. 11 and proceeds to run through the steps of FIG. 11.

In one example of the trigger assume that the ADC value for x(k) is greater than the primary threshold, the current state is monitoring, x(k) for the current triggering sample=3,200, the primary threshold=3,019, the average ADC value $\bar{x}(k)$ for the current triggering sample=2,000, and the average variance for the current triggering sample Var(k)=1,800. Applying the algorithm to the example, because x(k) is greater than the primary the threshold, mean__1 of the current triggering sample will be set to 2,000, the variance__1 of the current triggering sample will be set to 1,800, the F-test-counter will be reset to zero, the variance counter will be reset to zero, and the window counter will be reset to zero. The algorithm will then enter the droplet detection state and return to location 190 of FIG. 11. However, if in the example the current state is not monitoring, then the algorithm will either proceed through location step 210 to location step 210 of FIG. 13 if the method is in the droplet detection state, or proceed through location step 212 to location step 212 of FIG. 14 if the method is not in the droplet detection state.

The trigger transition state portion of the algorithm, as outlined above, looks for a droplet formation event, which is a point in time at which the onset of droplet formation is likely to have occurred, that is manifested by a discontinuity in the form of a sudden increase in the instantaneous or current sensor ADC signal. The use of triggering is critical to distinguish between a stuck droplet profile, as shown in FIGS. 6-9, and the circumstance in which the air sensor signal is elevated due to the presence of clinging air bubbles at the air-in-line sensor 116. If, for example, a trigger is not used, clinging air bubbles will lead to a significant number of false positives. While two different triggers are disclosed above to detect the onset of a droplet formation, in other embodiments, the event can be detected through a difference or derivative calculation, an F-test based upon a comparison of signal means through time, a signal exceeding a confidence interval surrounding an estimate of the mean, an increase that is beyond the projected/predicted signal, or through other mechanisms. The fundamental problem addressed in the instant disclosure is that of edge detection. For example, in one embodiment an exponentially weighted moving average can be used to establish the signal mean and variance. If a given sample is beyond the upper end of the 99% confidence interval a triggering event may be designated. In other embodiments, varying methods, such as a difference or derivative calculation, may be utilized to detect the edge of a stuck droplet.

As shown in FIG. 13, the droplet detection state occurs during steps 210 and 224-236. The droplet detection state is used to determine whether or not the measured air sensor ADC signal transitions in a manner consistent with droplet formation. The algorithm evaluates conditions to determine whether or not the signal transitions to a lower value that is stable through time in order to determine if a stuck droplet has formed. Detection of the stuck droplet formation occurs when the signal is stationary between the primary and secondary thresholds. If the signal is higher than the primary threshold, a droplet search is not required since it is detected as being air. After location step 210, in step 224 the method proceeds to increment the F-test and window counters each by one.

After step 224, the method proceeds to step 226 in which a determination is made as to whether the window count is greater than 160. If a determination is made in step 226 that the window count is greater than 160, then the method proceeds to step 228 and enters the monitoring state. This is an exit condition in which the stuck droplet profile search is turned off if a droplet is not found within 2 ml of the triggering event. A conservative window size was selected compared to the variance window to prevent any droplets from being missed. The search is turned off to prevent nuisance alarms due to triggering even when it has been inappropriately triggered by a moving air bubble. Moving air bubbles may have a similar triggering pattern as a stuck droplet. However, it is expected that the droplet alarm will not occur since the ADC signal would fall below the secondary threshold or the signal would be stable due to moving air bubbles. After step 228, the method then proceeds through location step 190 back to location step 190 of FIG. 11 and proceeds to run through the steps of FIG. 11.

If a determination is made in step 226 that the window count is not greater than 160, then the method proceeds to step 230. In step 230, a determination is made if the ADC value of x(k) of the current sample is less than the secondary threshold. If a determination is made in step 230 that the ADC value of x(k) of the current sample is less than the secondary threshold, then the method proceeds to step 228 and enters the monitoring state. For instance, in an example in which the secondary threshold=2,367 and x(k)=2,000, the method would enter the monitoring state. This is another exit condition in which a determination is made that the signal is not consistent with a struck droplet because the observed air sensor ADC value dropped below the minimum level observed for stuck droplets. After step 228, the method then proceeds through location step 190 back to location step 190 of FIG. 11 and proceeds to run through the steps of FIG. 11.

If a determination is made in step 230 that the ADC value of x(k) of the current sample is not less than the secondary threshold, then the method proceeds to step 232. In step 232, a determination is made if the average ADC value $\bar{x}(k)$ is less than the primary threshold. If a determination is made in step 232 that the average ADC value $\bar{x}(k)$ is not less than the primary threshold, then the method proceeds through location step 190 back to location step 190 of FIG. 11 and proceeds to run through the steps of FIG. 11. This represents that the sample of air which has moved past the sensor prior to the triggering event is significant (greater than or equal to 150 ul). Therefore, the triggering event could not have been due to an air bubble and further droplet count testing is not necessary. If a determination is made in step 232 that the average ADC value $\bar{x}(k)$ is less than the primary threshold, then the method proceeds to step 234.

In step 234, a determination is made if the average ADC value $\bar{x}(k)$ is greater than the secondary threshold. If a determination is made in step 234 that the average ADC value $\bar{x}(k)$ is not greater than the secondary threshold, then the method proceeds through location step 190 back to location step 190 of FIG. 11 and proceeds to run through the steps of FIG. 11. If a determination is made in step 234 that the average ADC value $\bar{x}(k)$ is greater than the secondary threshold, then the method proceeds to step 236.

In step 236, the droplet count state is entered and the variance counter is reset to zero. This occurs because the average sensor ADC level is between the primary threshold and the secondary threshold. For example, if the secondary threshold=2,367, the primary threshold=3,019, and the average ADC value $\bar{x}(k)$=2,400, then the droplet count state will be entered and the variance counter will be reset. After step 236, the method proceeds through location step 190 back to location step 190 of FIG. 11 and proceeds to run through the steps of FIG. 11.

As shown in FIG. 14, the droplet count state occurs during steps 212 and 238-260, and the alarm state occurs during step 262. The droplet count state implements the stability criterion for signals that are within the target range of stuck droplets and provides an alarm condition after 40 (500 μL) consecutive stable ADC observations. If the signal is not stable, the counter is reset. In addition, several exit conditions are used to change states if the signal moves outside the target range or if the signal has been unstable for a long period of time. After location step 212, the method proceeds to step 238 during which it increments the F-test and window counters each by one. After step 238, the method proceeds to step 240 during which it determines if the F-test counter, comprising the number of samples after the triggering event, is equal to fourteen. If a determination is made in step 240 that the F-test counter is equal to fourteen samples after the triggering event, then the method proceeds to step 242. The duration of time prior to the execution of the criteria was set to 14 samples (175 ul) after the triggering event in an effort to prevent the elimination due to any condition which could lead to a stuck droplet. However, the sample size could equal the duration of the signal above the primary threshold (up to a preset limit) plus the window size (which could be 12 in one example or various sizes in other examples).

In step 242, a variance test is applied during which a determination is made as to whether both variance_1 is less than the variance threshold, and also whether variance_2 is less than the variance threshold. Variance_1 is the average variance Var(k) which was saved for the triggering event sample. Variance_2 is the average variance Var(k) which was calculated for 14 samples after the triggering event sample in which k=k for the triggering event sample+14. The variance threshold=10,000. In other embodiments, varying values may be used for the variance threshold.

If in step 242 a determination is made that both variance_1 is less than the variance threshold and also that variance_2 is less than the variance threshold, then the method proceeds to step 244. In step 244, a F-test is applied during which a determination is made as to whether mean_2 is less than or equal to mean_1, or whether F is less than F critical. Mean_1 is the average ADC value $\bar{x}(k)$ which was saved for the triggering event sample. Mean_2 is the average ADC value $\bar{x}(k)$ which was calculated for 14 samples after the triggering event sample in which k=k for the triggering event sample+14. F is calculated using the formula $F=n*(mean\_1-mean\_2)^2/(var\_1+var\_2)^2$ with n being the total number of samples. F critical is determined based upon a F-distribution table commonly found in the literature for example, "Statistics for Experimenters," by George E. P. Box, William G. Hunger, and J. Stuart Hunter, 1978, John Wiley & Sons, Inc, page 638, which is hereby incorporated by reference.

In one embodiment, n=14, p=0.5, and F critical=4.3. In other embodiments, the values of these variables may vary. If in step 244 a determination is made that either mean_2 is less than or equal to mean_1, or that F is less than F critical, then the method proceeds to step 246 and the monitoring state is entered. This exit condition is as a result of the algorithm determining that there is not a stuck fluid droplet. For instance, if mean_2 is less than or equal to mean_1, this indicates that an air bubble moved past the sensor and washed away some of the air bubbles lodged in front of the sensor. Therefore, in this case the droplet search is disabled. This portion of the algorithm was introduced to eliminate false alarms due to false triggering events such as micro air bubbles. After step 246, the method then proceeds through location step 190 back to location step 190 of FIG. 11 and proceeds to run through the steps of FIG. 11.

As one example of one embodiment of the F-test, assume that n=14, p=0.5, F critical=4.3, F-test counter=14, variance_1=8,000, variance_2=9,000, mean_1=2,000, and mean_2=2,050. F is then determined under the algorithm to be $F=14*(mean\_1-mean\_2)^2/(variance\_1+variance\_2)=14*(2,000-2,050)^2/(8,000+9,000)=2.1$. Because F=2.1 is less than F critical=4.3, under the algorithm the state transitions to monitoring. As a second example of another embodiment of the F-test, assume that n=14, p=0.5, F critical=4.3, F-test counter=14, variance_1=8,000, variance_2=9,000, mean_1=2,000, and mean_2=2,100. Under the algorithm, F is determined to be $F=14*(mean\_1-mean\_2)^2/(variance\_1+variance\_2)=14*(2,000-2,100)^2/(8,000+9,000)=8.2$.

Because F=8.2 is not less than F critical=4.3, under the algorithm the state does not transition to monitoring. As a third example, assume that F-test counter=14, variance_1=8,000, variance_2=9,000, mean_1=2,000, and mean_2=1,900. Under the algorithm, mean_2=1,900 is less than mean_1=2,000. As a result, under the algorithm the state transitions to monitoring.

Figure 16:
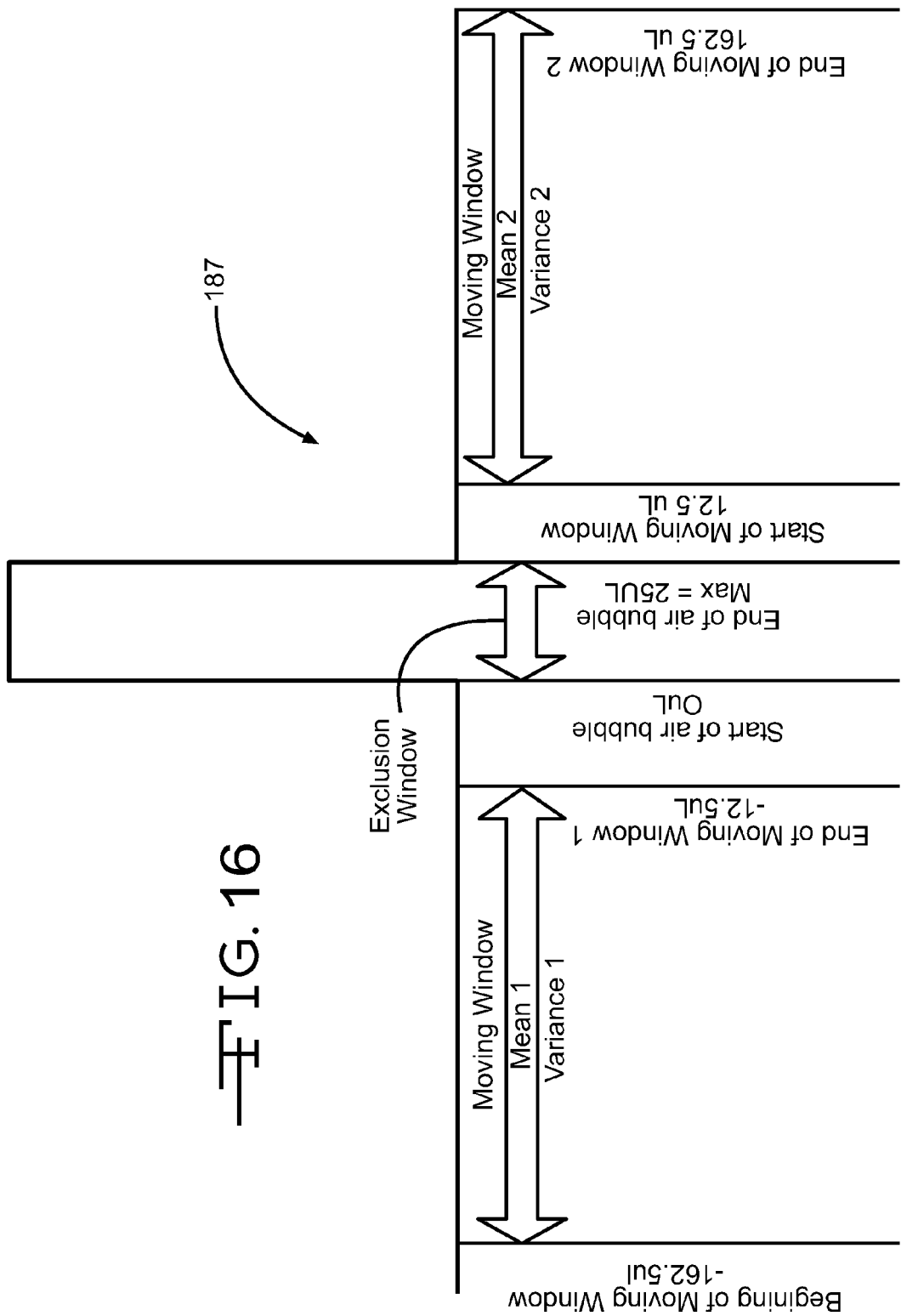
FIG. 16 is a diagram illustrating one embodiment of moving window calculations related to the F-test for false positive rejections under the algorithm.

FIG. 16 is a diagram 187 illustrating one embodiment of moving window calculations related to the F-test of step 244 of FIG. 14 for false positive rejections under the algorithm. A triggering event occurs at the start of the air bubble which leads to the calculation of mean_1 and variance_1 on the basis of the window of samples preceding the event. After 25 uL (or two samples) have passed the air sensor, a 12 sample window is initiated. At the conclusion of this period, mean_2 and variance_2 are calculated and the F-test criteria are executed.

Figure 17:
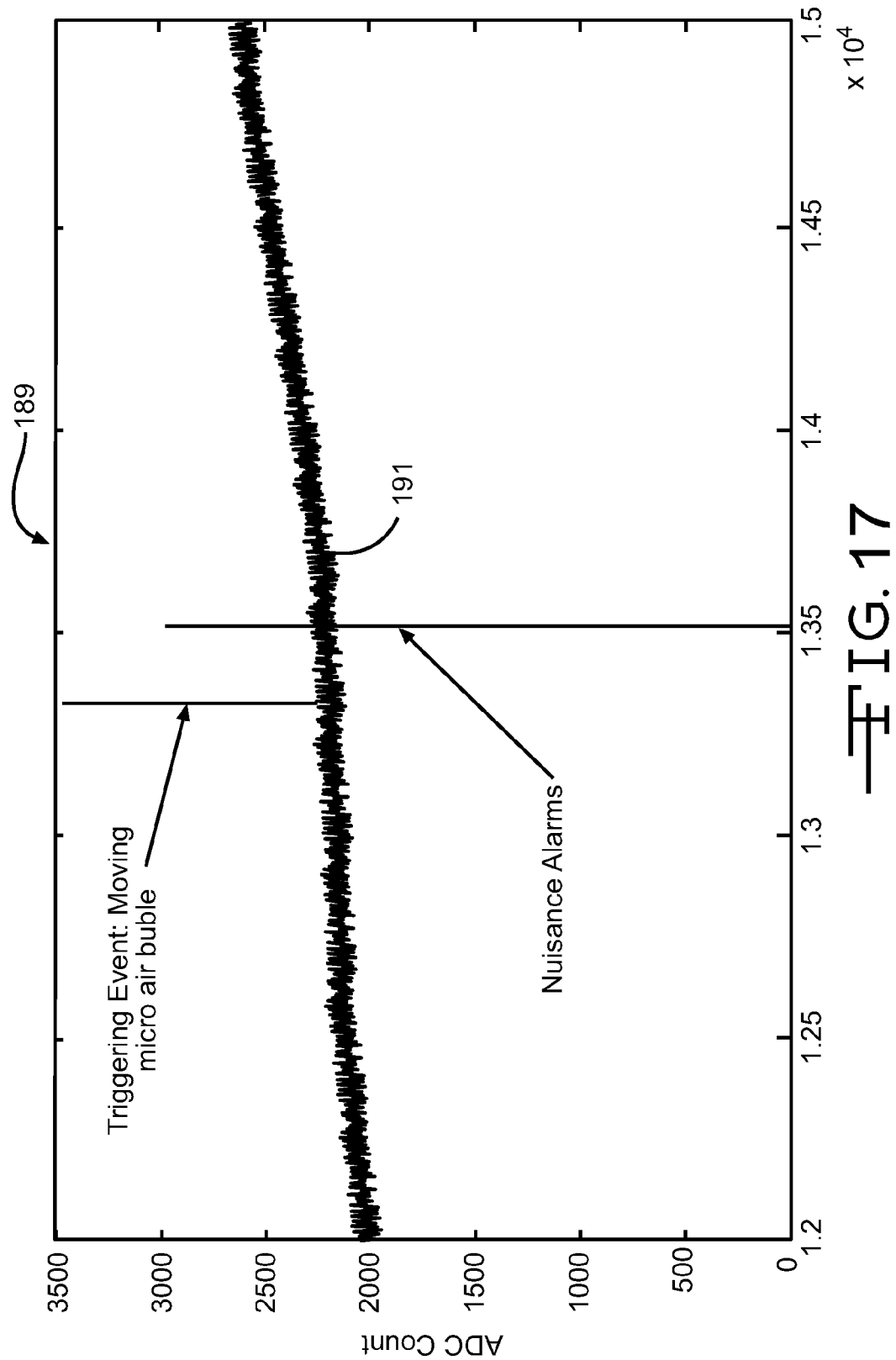
FIG. 17 is a graph plotting air-sensor ADC values versus sample number illustrating one embodiment of a laboratory-observed signal pattern that is rejected under an F-test as being a stuck fluid droplet.

FIG. 17 is a graph 189 plotting air-sensor ADC values versus sample number illustrating one embodiment of a laboratory-observed signal pattern 191 that is rejected under an F-test portion of step 244 of the algorithm of FIG. 14 as being a stuck fluid droplet. For this particular embodiment, the F-test portion of the algorithm will determine that it is a false positive and will put the algorithm back into the monitoring state. However, when moving air bubbles lead to an air sensor signal that is above the secondary threshold, a nuisance air-in-line alarm may occur. Only specific profiles known to be caused by air bubbles and not due to stuck droplets lead to elimination from the stuck droplet search. If the profile could be caused by a struck droplet and/or a moving air bubble, the profile is not eliminated since the risk to the health of the patient is higher due to a stuck droplet.

If a determination is made in step 240 of FIG. 14 that the F-test counter is not equal to fourteen, then the method proceeds directly to step 248. Similarly, if a determination is made in step 242 that either variance_1 is greater than the variance threshold or that variance_2 is greater than the variance threshold, then the method proceeds directly to step 248. This is because a high-variance value suggests a heteroscadastic signal that may violate F-test criteria. As a result, the F-test is only carried out when the variances are within the specified range. Also, if a determination is made in step 244 that mean_2 is not less than or equal to mean_1, and that F is not less than F critical, then the method proceeds directly to step 248. It is noted that if mean_2 is greater than mean_1, two possible scenarios are possible as follows: (1) a stuck droplet event occurred; or (2) an air bubble moved past the sensor and at the same time tiny air bubbles got stuck in front of the sensor. The profiles of these two events are identical. In this case, the droplet search is not disabled. Therefore, the droplet search could lead to some nuisance alarms to prevent potential harm to the patient. In step 248, a determination is made as to whether the window count is greater than 160. If a determination is made in step 248 that the window count is greater than 160, then the method proceeds to step 246 and the monitoring state is entered. This exit condition is as a result of the algorithm determining that there is not a stuck fluid droplet. After step 246, the method then proceeds through location step 190 back to location step 190 of FIG. 11 and proceeds to run through the steps of FIG. 11.

If a determination is made in step 248 that the window count is not greater than 160, than the method proceeds to step 250. In step 250, a determination is made as to whether x(k) is less than the secondary threshold. If a determination is made in step 250 that x(k) is less than the secondary threshold, then the method proceeds to step 246 and the monitoring state is entered. This exit condition occurs because the algorithm determines that there is not a stuck droplet. After step 246, the method then proceeds through location step 190 back to location step 190 of FIG. 11 and proceeds to run through the steps of FIG. 11.

If a determination is made in step 250 that x(k) is not less than the secondary threshold, then the method proceeds to step 252. In step 252, a determination is made as to whether the average ADC value $\bar{x}(k)$ is less than the primary threshold plus the hysteresis. The hysteresis is set in one embodiment at forty-one. In other embodiments, the hysteresis may be varied. If a determination is made in step 252 that the average ADC value $\bar{x}(k)$ is not less than the primary threshold plus the hysteresis, then the method proceeds to step 254. In step 254 the droplet detection state is entered. As an example, if in one embodiment the primary threshold=3,019 then any average ADC value $\bar{x}(k)$ which is greater than or equal to 3,060 will cause entry into the droplet detection state. After step 254, the method proceeds through location step 190 back to location step 190 of FIG. 11 and proceeds to run through the steps of FIG. 11.

Figure 18:
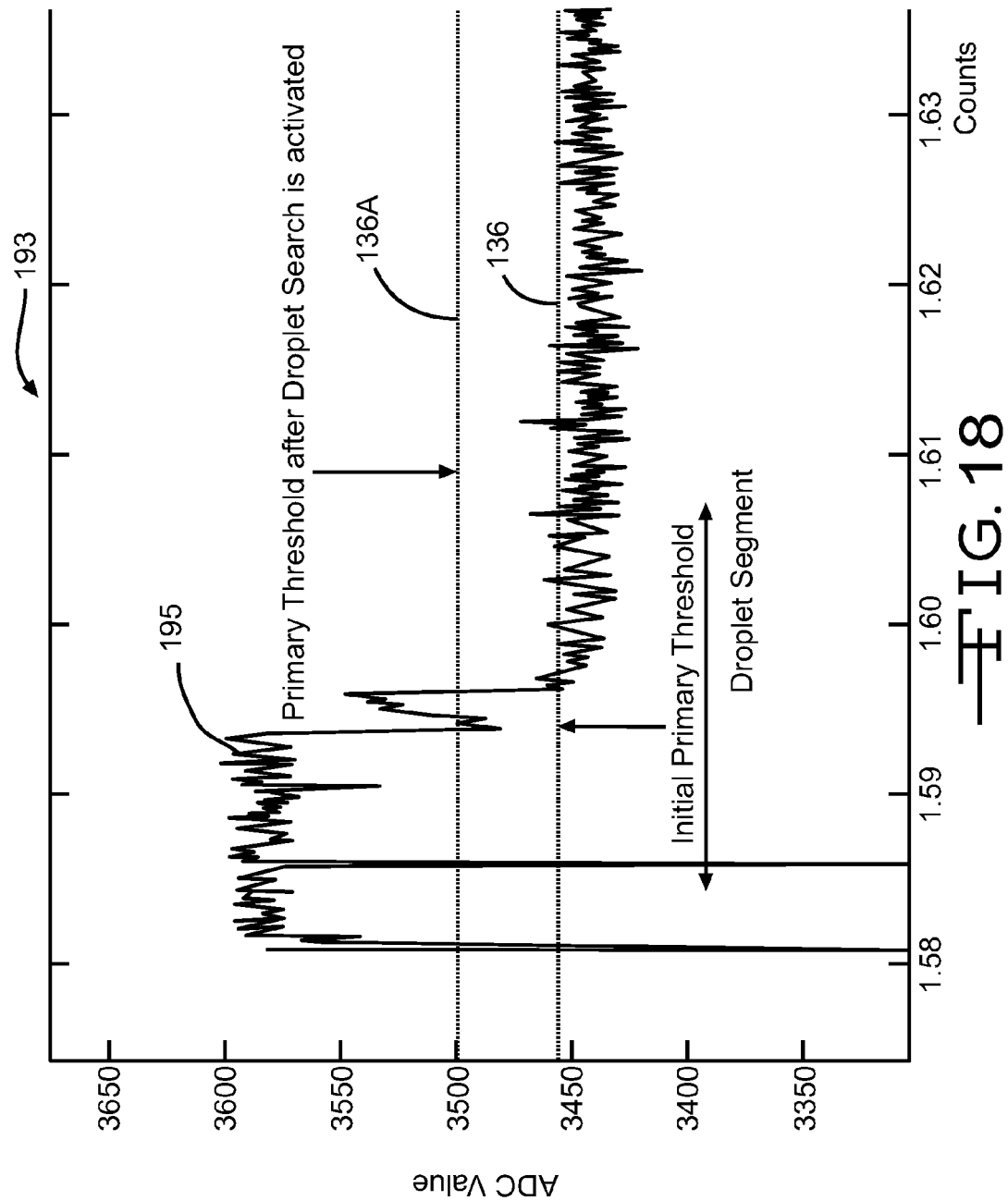
FIG. 18 is a graph plotting air-sensor ADV values versus counts illustrating another embodiment of a laboratory-observed signal pattern applying a hysteresis threshold above a primary threshold.

FIG. 18 is a graph 193 plotting air-sensor ADV values versus counts illustrating another embodiment of a laboratory-observed signal pattern 195 applying a hysteresis threshold 136A above a primary threshold 136 for one embodiment of step 252 of FIG. 14. As shown in FIG. 18, it is possible to generate a stuck droplet where the ADC value oscillates around the primary threshold 136. Since the ADC value is oscillating around the primary threshold 136, it could bypass single bubble and cumulative alarms as well as the stuck droplet detection system. Using an increased hysteresis threshold 136A eliminates this problem by increasing the ADC value that must be crossed for the transition from droplet count state to the droplet detection state.

If a determination is made in step 252 of FIG. 14 that the average ADC value $\bar{x}(k)$ is less than the primary threshold plus the hysteresis, then the method proceeds to step 256. In step 256, a determination is made as to whether variance(k) for the current sample is less than the variance threshold. As previously detailed, the variance threshold is set at 10,000. In other embodiments, the variance threshold may vary. If a determination is made in step 256 that variance(k) is not less than the variance threshold, then the method proceeds through location step 190 back to location 190 of FIG. 11 and proceeds to run through the steps of FIG. 11.

If a determination is made in step 256 that variance(k) is less than the variance threshold, then the method proceeds to step 258. In step 258, the variance counter is incremented by one. The variance threshold comparison tests for stability. It indicates if the ADC count has been stable for 500 uL. Instability does not eliminate searching but delays an alarm due to a stuck droplet. As seen in the droplet profiles, stability is achieved in the droplet after a triggering event. The length of the triggering event is variably as is the time taken for the ADC value to become stable. As previously mentioned, the variance threshold used for this algorithm is 10,000 (value obtained empirically from experimental results). A large value was selected since considerable variations were seen in the droplet profile. A larger value than this number would be indicative of a significant jump in ADC which cannot occur if the profile is caused by a droplet. After step 258, the method proceeds to step 260. In step 260, a determination is made as to whether the variance count is greater than forty. If in step 260 the variance count is determined to not be greater than 40, then the method proceeds through location step 190 back to location 190 of FIG. 11 and proceeds to run through the steps of FIG. 11.

If in step 260 the variance count is determined to be greater than 40, then the method proceeds to step 262 and sounds the air alarm that too much air is in the fluid delivery line 104. At this point in time, the drug delivery infusion system 100 of FIG. 1 shuts down the pumping device 106 to avoid air from being pumped into the patient. The drug delivery infusion system 100 also communicates to medical personnel that air has been detected.

Although the algorithm described above provides the best known realization of the invention, other methods have been discovered by Applicant which exploit the key findings previously disclosed to detect the droplet formation event. For example, noting that the triggering event is dominated by high frequency signal components enables a spectral analysis to differentiate the response of the system to: (1) air bubbles; (2) froth; (3) air-in-line; and (4) air-in-line with a stuck droplet. Alternately, a comparison of two or more low-pass filtered or averaged signals could be used to differentiate the triggering event and subsequent signal stability. For example, two low pass filters, each with different break frequencies, provide a means for: (1) detecting the trigger event; (2) estimating signal stability; and (3) detecting entry into the droplet detection state above. The two different filters can be implemented using the moving average previously described with averaging windows set to twelve and twenty-four respectively. Additionally, pattern matching or classification can be employed to identify and distinguish air from fluid amid stuck droplets on the basis of the features identified previously or by using a supervised clustering or classification approach (for example, kth-nearest neighbor, discriminant analysis, k-means, artificial neural networks, classification and regression trees, Bayesian networks, or decision trees). Such classification systems exploit the key elements disclosed previously by operating on at least two successive features, observed through time, and extracted from the air-in-line sensor system signal. In other embodiments, varying algorithms and mechanisms may be utilized to determine the existence of a struck fluid droplet.

The instant disclosure allows for the presence of a stuck fluid droplet, stuck over a sensor in an infusion delivery system, to be determined based upon a pattern relationship connecting the physical formation of a stuck fluid droplet to the temporal air sensor signal through time. The disclosure improves the air detection capability of existing infusion pump systems that rely on sensors to make a real-time assessment. In doing so, the disclosure does not require additional hardware modifications but instead leverages the acquired sensor voltage signal. Additionally, the disclosure does not necessarily replace existing software modules for air detection but adds an additional safety layer. The disclosure provides for a multi-state method for detecting the presence of a stuck droplet on the basis of its formation as manifested in the unique transient characteristics of the air sensor signal. The pattern recognition software component of the disclosure identifies a stuck droplet formation event. The stuck droplet detection confirmation algorithm of the disclosure requires a specific and bounded transient behavior following a detected event. The false-positive rejection algorithm of the disclosure is able to distinguish between stuck droplet formation and an air bubble accumulation/purge event.

The adaptive algorithm of the disclosure includes multiple parameters that are adjusted based upon the estimated dynamic range of the air sensor system. The dynamic range of the air sensor system is initially established through a calibration procedure in the factory. However under the disclosure the range of the air sensor system, including air-in-line thresholds, is adapted according to air actual sensor readings through time which enables robustness over calibration errors, fluid delivery line types, and varying circumstances such as variances in temperature. This is done without requiring hardware modifications or significant updates to prior calibration methodologies.

It should be understood, of course, that the foregoing relates to exemplary embodiments of the disclosure and that modifications may be made without departing from the scope of the following claims.

We claim:

1. An infusion system comprising:
a pump;
a fluid delivery line connected to the pump for delivering fluid;
at least one sensor connected to the fluid delivery line for emitting and receiving signals to detect whether there is air in the fluid delivery line;
a processor in electronic communication with the pump and the at least one sensor; and
a memory in electronic communication with the processor, wherein the memory comprises programming code for execution by the processor, and the programming code is configured to analyze the signals to determine if a stuck fluid droplet is stuck within the fluid delivery line at a location of the at least one sensor;
wherein the programming code is configured to determine if the stuck fluid droplet is stuck within the fluid delivery line at the location of the at least one sensor by determining a pattern relationship over time between a plurality of digital measurements of the signals;
wherein the programming code is configured to determine that the stuck fluid droplet is present if the determined pattern relationship starts at or below a known liquid signal ADC value at a first period in time, increases from at or below the known liquid signal ADC value to over a primary threshold ADC value at a second period in time, decreases from over the primary threshold ADC value to between the primary threshold ADC value and a secondary threshold ADC value at a third period in time, and passes a stability test while being disposed at a fourth period in time between the primary threshold ADC value and the secondary threshold ADC value.

2. The infusion system of claim 1 wherein the programming code is configured to determine if the stuck fluid droplet is stuck within the fluid delivery line at the location of the at least one sensor by comparing the determined pattern relationship over time to a programmed pattern over time algorithm which is indicative of the presence of the stuck fluid droplet.

3. The infusion system of claim 1 wherein the programming code is configured to analyze the plurality of digital measurements over multiple differently programmed states to determine the pattern relationship.

4. The infusion system of claim 3 wherein the multiple differently programmed states, programmed in the programming code, comprise a monitoring state, a trigger transition state, a droplet detection state, and a droplet count state.

5. The infusion system of claim 3 wherein the programming code is programmed so that during a monitoring state the digital measurements of the signals are taken, average ADC values and average variance values of the signals are calculated, and the monitoring state transitions to a trigger transition state.

6. The infusion system of claim 3 wherein the programming code is programmed so that during a trigger transition state, depending on the digital measurements of the signals, on a state status, and on comparisons of the measurements of the signals to thresholds, the transition state transitions to either a monitoring state, a droplet detection state, or a droplet count state.

7. The infusion system of claim 3 wherein the programming code is programmed so that during a droplet detection state, depending on the digital measurements of the signals, and on comparisons of the measurements and average ADC values of the signals to thresholds, the droplet detection state either transitions to a monitoring state or enters a droplet count state.

8. The infusion system of claim 3 wherein the programming code is programmed so that during a droplet count state, depending on the digital measurements of the signals, and on comparisons of the measurements, average ADC values of the signals, and average variances of the signals to thresholds, the droplet count state either transitions to a monitoring state, enters a droplet detection state, or signals an alarm.

9. The infusion system of claim 1 wherein the programming code is configured to determine during the stability test that the stuck fluid droplet is not present if the signals during the fourth period in time vary more than a set amount, drop down to or below a previously observed fluid level, drop below the secondary threshold ADC value, or increase over the primary threshold ADC value.

10. The infusion system of claim 1 wherein the programming code is configured to determine during a triggering state, representing the possible beginning of the stuck fluid droplet, whether an ADC value of one of the digital measurements exceeds a primary threshold ADC value, or is less than a trigger threshold ADC value but greater than a minimum ADC value, and if so analyzes the digital measurements of the signals further to determine if the stuck fluid droplet is present, and if not determines that a stuck fluid droplet is not present.

11. The infusion system of claim 1 wherein the programming code is configured to determine ADC mean values for the signals to determine the pattern relationship.

12. The infusion system of claim 1 wherein the programming code is configured to conduct a test for false positives, indicating that the stuck fluid droplet is not present, by calculating and comparing at different times at least one of ADC mean values, variance mean values, or F critical calculations for the digital measurements.

13. The infusion system of claim 1 wherein the programming code is configured to dynamically calibrate the at least one sensor during fluid delivery based on real-time measurements of the signals.

14. The infusion system of claim 13 wherein the programming code is configured to update a dynamic range of the real-time measurements of the signals with the dynamic range ranging between a minimum recorded measurement of the signals and a maximum recorded measurement of the signals.

15. A method for detecting a stuck fluid droplet in a fluid delivery line of an infusion system comprising the steps of:
pumping fluid through the fluid delivery line over at least one sensor;
emitting and receiving signals from the at least one sensor into and from the fluid delivery line; and
processing measurements of the signals, using a processor, to determine whether a stuck fluid droplet is stuck within the fluid delivery line at a location of the at least one sensor;
wherein the step of processing measurements of the signals with the processor further comprises determining whether the stuck fluid droplet is stuck within the fluid delivery line at the location of the at least one sensor by determining a pattern relationship over time between a plurality of digital measurements of the signals;
wherein the step of processing measurements of the signals with the processor further comprises determining that the stuck fluid droplet is present if the determined pattern relationship starts at or below a known liquid signal ADC value at a first period in time, increases from at or below the known liquid signal ADC value to over a primary threshold ADC value at a second period in time, decreases from over the primary threshold ADC value to between the primary threshold ADC value and a secondary threshold ADC value at a third period in time, and passes a stability test while being disposed at a fourth period in time between the primary threshold ADC value and the secondary threshold ADC value.

16. The method of claim 15 wherein the step of processing measurements of the signals with the processor further comprises comparing the determined pattern relationship over time to a programmed pattern over time algorithm which is indicative of the presence of the stuck fluid droplet.

17. The method of claim 15 wherein the step of processing measurements of the signals with the processor further comprises analyzing the plurality of digital measurements over multiple differently programmed states, programmed in the processor, to determine the pattern relationship.

18. The method of claim 17 wherein the multiple differently programmed states programmed in the processor comprise a monitoring state, a trigger transition state, a droplet detection state, and a droplet count state.

19. The method of claim 17 wherein the step of processing measurements of the signals with the processor further comprises, during a monitoring state, taking the digital measurements of the signals, calculating average ADC values and average variance values of the signals, and transitioning from the monitoring state to a trigger transition state.

20. The method of claim 17 wherein the step of processing measurements of the signals with the processor further comprises, during a trigger transition state, depending on the digital measurements of the signals, on a state status, and on comparisons of the measurements of the signals to thresholds, transitioning from the trigger transition state to either a monitoring state, a droplet detection state, or a droplet count state.

21. The method of claim 17 wherein the step of processing measurements of the signals with the processor further comprises, during a droplet detection state, depending on the digital measurements of the signals, and on comparisons of the measurements and average ADC values of the signals to thresholds, either transitioning from the droplet detection state to a monitoring state or entering a droplet count state.

22. The method of claim 17 wherein the step of processing measurements of the signals with the processor further comprises, during a droplet count state, depending on the digital measurements of the signals, and on comparisons of the measurements, average ADC values of the signals, and average variances of the signals to thresholds, either transitioning from the droplet count state to a monitoring state, entering a droplet detection state, or signaling an alarm.

23. The method of claim 15 wherein the step of processing measurements of the signals with the processor further comprises determining during the stability test that the stuck fluid droplet is not present if the signals during the fourth period in time vary more than a set amount, drop down to or below a previously observed fluid level, drop below the secondary threshold ADC value, or increase over the primary threshold ADC value.

24. The method of claim 15 wherein the step of processing measurements of the signals with the processor further comprises determining during a triggering state, representing the possible beginning of the stuck fluid droplet, whether an ADC value of one of the digital measurements exceeds a primary threshold ADC value, or is less than a trigger threshold ADC value but greater than a minimum ADC value, and if so analyzes the digital measurements of the signals further to determine if the stuck fluid droplet is present, and if not determines that a stuck fluid droplet is not present.

25. The method of claim 15 wherein the step of processing measurements of the signals with the processor further comprises determining ADC mean values for the signals to determine the pattern relationship.

26. The method of claim 15 wherein the step of processing measurements of the signals with the processor further comprises conducting a test for false positives, indicating that the stuck fluid droplet is not present, by calculating and comparing at different times at least one of ADC mean values, variance mean values, or F critical calculations for the digital measurements.

27. The method of claim 15 wherein the step of processing measurements of the signals with the processor further comprises dynamically calibrating the at least one sensor during the pumping of the fluid through the fluid delivery line based on real-time measurements of the signals.

28. The method of claim 27 wherein the step of processing measurements of the signals with the processor further comprises updating a dynamic range of the real-time measurements of the signals with the dynamic range ranging between a minimum recorded measurement of the signals and a maximum recorded measurement of the signals.

29. A method for detecting air in a fluid delivery line of an infusion system comprising the steps of:
pumping fluid through the fluid delivery line over at least one sensor;
emitting and receiving signals from the at least one sensor into and from the fluid delivery line; and
processing measurements of the signals, using a processor, to determine whether the air is in the fluid delivery line by determining a pattern relationship over time of the signals while the signals are below an air/liquid threshold ADC value boundary;
wherein the step of processing measurements of the signals with the processor further comprises determining that the air is present if the determined pattern relationship starts at or below a known liquid signal ADC value at a first period in time, increases from at or below the known liquid signal ADC value to over the air/liquid threshold ADC value boundary at a second period in time, decreases from over the air/liquid threshold ADC value boundary to between the air/liquid threshold ADC value boundary and a secondary threshold ADC value at a third period in time, and passes a stability test while being disposed at a fourth period in time between the air/liquid threshold ADC value boundary and the secondary threshold ADC value.

30. The method of claim 29 wherein the step of processing measurements of the signals with the processor further comprises comparing the determined pattern relationship over time to a programmed pattern over time algorithm which is indicative of the presence of the air being present in the fluid delivery line.

31. The method of claim 29 wherein the step of processing measurements of the signals with the processor further comprises analyzing the plurality of measurements over multiple differently programmed states, programmed in the processor, to determine the pattern relationship.

32. The method of claim 31 wherein the multiple differently programmed states programmed in the processor comprise a monitoring state, a trigger transition state, a detection state, and a count state.

33. The method of claim 29 wherein the step of processing measurements of the signals with the processor further comprises, during a monitoring state, taking the measurements of the signals, calculating average ADC values and average variance values of the signals, and transitioning from the monitoring state to a trigger transition state.

34. The method of claim 29 wherein the step of processing measurements of the signals with the processor further comprises, during a trigger transition state, depending on the measurements of the signals, on a state status, and on comparisons of the measurements of the signals to thresholds, transitioning from the trigger transition state to either a monitoring state, a detection state, or a count state.

35. The method of claim 29 wherein the step of processing measurements of the signals with the processor further comprises, during a detection state, depending on the measurements of the signals, and on comparisons of the measurements and average ADC values of the signals to thresholds, either transitioning from the detection state to a monitoring state or entering a count state.

36. The method of claim 29 wherein the step of processing measurements of the signals with the processor further comprises, during a count state, depending on the measurements of the signals, and on comparisons of the measurements, average ADC values of the signals, and average variances of the signals to thresholds, either transitioning from the count state to a monitoring state, entering a detection state, or signaling an alarm.

37. The method of claim 29 wherein the step of processing measurements of the signals with the processor further comprises determining during the stability test that the air is not present if the signals during the fourth period in time vary more than a set amount, drop down to or below a previously observed fluid level, drop below the secondary threshold ADC value, or increase over the air/liquid threshold ADC value boundary.

38. The method of claim 29 wherein the step of processing measurements of the signals with the processor further comprises determining during a triggering state, representing the possible beginning of the air, whether an ADC value of one of the measurements exceeds the air/liquid threshold ADC boundary, or is less than a trigger threshold ADC value but greater than a minimum ADC value, and if so analyzes the measurements of the signals further to determine if the air is present, and if not determines that air is not present.

39. The method of claim 29 wherein the step of processing measurements of the signals with the processor further comprises determining ADC mean values for the signals to determine the pattern relationship.

40. The method of claim 29 wherein the step of processing measurements of the signals with the processor further comprises conducting a test for false positives, indicating that the air is not present, by calculating and comparing at different times at least one of ADC mean values, variance mean values, or F critical calculations for the measurements.

41. The method of claim 29 wherein the step of processing measurements of the signals with the processor further comprises dynamically calibrating the at least one sensor during the pumping of the fluid through the fluid delivery line based on real-time measurements of the signals.

42. The method of claim 41 wherein the step of processing measurements of the signals with the processor further comprises updating a dynamic range of the real-time measurements of the signals with the dynamic range ranging between a minimum recorded measurement of the signals and a maximum recorded measurement of the signals.

* * * * *